United States Patent
Lu

(10) Patent No.: US 12,064,183 B2
(45) Date of Patent: Aug. 20, 2024

(54) METHODS, APPARATUSES AND STORAGE MEDIUMS FOR ABLATION PLANNING AND PERFORMANCE

(71) Applicant: Canon U.S.A., Inc., Melville, NY (US)

(72) Inventor: Zhimin Lu, Chelmsford, MA (US)

(73) Assignee: Canon U.S.A., Inc., Melville, NY (US)

( * ) Notice: Subject to any disclaimer, the term of this patent is extended or adjusted under 35 U.S.C. 154(b) by 755 days.

(21) Appl. No.: 16/492,916

(22) PCT Filed: Mar. 2, 2018

(86) PCT No.: PCT/US2018/020752
§ 371 (c)(1),
(2) Date: Sep. 10, 2019

(87) PCT Pub. No.: WO2018/175094
PCT Pub. Date: Sep. 27, 2018

(65) Prior Publication Data
US 2020/0008875 A1    Jan. 9, 2020

Related U.S. Application Data

(60) Provisional application No. 62/474,265, filed on Mar. 21, 2017.

(51) Int. Cl.
*A61B 34/10* (2016.01)
*A61B 18/00* (2006.01)
(Continued)

(52) U.S. Cl.
CPC .............. *A61B 34/10* (2016.02); *A61B 18/02* (2013.01); *A61B 18/1815* (2013.01);
(Continued)

(58) Field of Classification Search
CPC ..... A61B 34/10; A61B 18/02; A61B 18/1815; A61B 2018/00577; A61B 2034/104;
(Continued)

(56) References Cited

U.S. PATENT DOCUMENTS 5,298,988 A    3/1994  Everett et al.
5,588,432 A *  12/1996 Crowley .............. A61B 5/6848
                                                        600/374
(Continued)

FOREIGN PATENT DOCUMENTS

DE    102013208897 A1    11/2014
EP         2846697 A1    11/2013
(Continued)

OTHER PUBLICATIONS

F. Caselles, et al., "A geometric model for active contours in image processing", Num. Mathematik, vol. 66, Issue 1, Jan. 1993, pp. 1-31.

(Continued)

*Primary Examiner* — Kathleen Y Dulaney
(74) *Attorney, Agent, or Firm* — Canon U.S.A., Inc. IP Division

(57) ABSTRACT

One or more devices, systems, methods and storage mediums for performing ablation planning and/or ablation performance are provided. Examples of applications for such devices, systems, methods and storage mediums include imaging, evaluating and diagnosing biological objects, such as, but not limited to, lesions and tumors, and such devices, systems, methods and storage mediums may be used for radiotherapy applications (e.g., to determine whether to place seed(s) for radiotherapy). Preferably, a medial axis or a center line for a predetermined biological object (e.g., a lesion or tumor) is determined/found, one or more target points are picked along the medial axis or center line, and the ablation or radiotherapy zones are defined and optimized. Security checks may be performed in one or more embodiments to ensure proper use of the equipment and patient information.

16 Claims, 20 Drawing Sheets

(51) Int. Cl.
  *A61B 18/02* (2006.01)
  *A61B 18/18* (2006.01)
  *A61B 90/00* (2016.01)
  *A61N 5/10* (2006.01)
  *G06T 7/00* (2017.01)
  *G06T 7/11* (2017.01)
  *G06T 7/68* (2017.01)
  *G16H 20/40* (2018.01)
  *G16H 30/40* (2018.01)

(52) U.S. Cl.
  CPC .......... *A61N 5/1039* (2013.01); *G06T 7/0012* (2013.01); *G06T 7/11* (2017.01); *G06T 7/68* (2017.01); *G16H 20/40* (2018.01); *G16H 30/40* (2018.01); *A61B 2018/00577* (2013.01); *A61B 2034/104* (2016.02); *A61B 2034/105* (2016.02); *A61B 2034/107* (2016.02); *A61B 2090/367* (2016.02); *A61B 2090/3735* (2016.02); *A61B 2090/374* (2016.02); *A61B 2090/3762* (2016.02); *G06T 2207/20101* (2013.01); *G06T 2207/20104* (2013.01); *G06T 2207/30004* (2013.01); *G06T 2207/30048* (2013.01); *G06T 2207/30172* (2013.01)

(58) Field of Classification Search
  CPC ........ A61B 2034/105; A61B 2034/107; A61B 2090/367; A61B 2090/3735; A61B 2090/374; A61B 2090/3762; A61B 6/03; A61N 5/1039; A61N 5/103; G06T 7/0012; G06T 7/11; G06T 7/68; G06T 2207/20101; G06T 2207/20104; G16H 20/40; G16H 30/40
  USPC ...................... 606/34; 382/128, 203; 600/424
  See application file for complete search history.

(56) References Cited

U.S. PATENT DOCUMENTS

| | | | | |
|---|---|---|---|---|
| 5,849,011 | A * | 12/1998 | Jones | A61B 18/1477 606/49 |
| 5,926,568 | A * | 7/1999 | Chaney | G06V 10/754 382/128 |
| 6,041,249 | A | 3/2000 | Regn | |
| 6,245,059 | B1 | 6/2001 | Clapham | |
| 6,341,036 | B1 | 1/2002 | Tearney et al. | |
| 6,363,134 | B1 | 3/2002 | Suzuki | |
| 6,505,065 | B1 | 1/2003 | Yanof et al. | |
| 6,605,095 | B2 | 8/2003 | Grossman | |
| 6,690,964 | B2 | 2/2004 | Bieger et al. | |
| 6,851,855 | B2 | 2/2005 | Mitschke et al. | |
| 7,127,802 | B1 | 10/2006 | Damadian et al. | |
| 7,200,251 | B2 * | 4/2007 | Joshi | G06T 17/20 703/2 |
| 7,302,288 | B1 | 11/2007 | Schellenberg | |
| 7,359,746 | B2 | 4/2008 | Arata | |
| 7,402,161 | B2 | 7/2008 | Zvuloni et al. | |
| 7,447,408 | B2 | 11/2008 | Bouma et al. | |
| 7,457,657 | B2 | 11/2008 | Harder | |
| 7,551,293 | B2 | 6/2009 | Yelin et al. | |
| 7,697,973 | B2 | 4/2010 | Strommer et al. | |
| 7,796,270 | B2 | 9/2010 | Yelin et al. | |
| 7,801,587 | B2 | 9/2010 | Webber et al. | |
| 7,859,679 | B2 | 12/2010 | Bouma et al. | |
| 7,872,759 | B2 | 1/2011 | Tearney et al. | |
| 7,889,348 | B2 | 2/2011 | Tearney et al. | |
| 8,045,177 | B2 | 10/2011 | Tearney et al. | |
| 8,050,471 | B2 | 11/2011 | Mielekamp et al. | |
| 8,145,018 | B2 | 3/2012 | Shishkov et al. | |
| 8,182,149 | B2 | 5/2012 | Haras | |
| 8,208,708 | B2 | 6/2012 | Homan et al. | |
| 8,289,522 | B2 | 10/2012 | Tearney et al. | |
| 8,290,225 | B2 | 10/2012 | Lobregt et al. | |
| 8,554,307 | B2 * | 10/2013 | Razzaque | A61B 8/483 600/407 |
| 8,666,128 | B2 | 3/2014 | Chaney et al. | |
| 8,670,816 | B2 * | 3/2014 | Green | A61B 17/221 600/424 |
| 8,693,760 | B2 | 4/2014 | Yokosawa et al. | |
| 8,798,227 | B2 | 8/2014 | Tsukagoshi et al. | |
| 8,838,213 | B2 | 9/2014 | Tearney et al. | |
| 8,928,889 | B2 | 1/2015 | Tearney et al. | |
| 9,125,689 | B2 | 9/2015 | Mielekamp | |
| 9,254,089 | B2 | 2/2016 | Tearney et al. | |
| 9,265,572 | B2 | 2/2016 | Fuchs et al. | |
| 9,295,391 | B1 | 3/2016 | Tearney et al. | |
| 9,332,942 | B2 | 5/2016 | Jaffer et al. | |
| 9,557,154 | B2 | 1/2017 | Tearney et al. | |
| 9,747,684 | B2 | 8/2017 | Trovato et al. | |
| 2004/0213444 | A1 | 10/2004 | Yamamichi | |
| 2004/0249270 | A1 * | 12/2004 | Kondo | G06T 7/12 382/128 |
| 2005/0033160 | A1 * | 2/2005 | Yamagata | A61B 6/12 600/425 |
| 2006/0023840 | A1 | 2/2006 | Boese | |
| 2006/0074413 | A1 * | 4/2006 | Behzadian | A61B 18/1477 606/41 |
| 2008/0033410 | A1 * | 2/2008 | Rastegar | A61B 34/30 606/9 |
| 2008/0091171 | A1 * | 4/2008 | Strommer | G06T 7/564 604/528 |
| 2009/0196480 | A1 * | 8/2009 | Nields | G06T 7/33 382/132 |
| 2009/0259960 | A1 | 10/2009 | Steinle et al. | |
| 2009/0287223 | A1 | 11/2009 | Pua et al. | |
| 2009/0318804 | A1 | 12/2009 | Avital et al. | |
| 2010/0063392 | A1 | 3/2010 | Nishina et al. | |
| 2010/0063496 | A1 * | 3/2010 | Trovato | A61B 90/36 606/34 |
| 2010/0092389 | A1 | 4/2010 | Jaffer | |
| 2010/0104068 | A1 | 4/2010 | Kilby et al. | |
| 2010/0172541 | A1 | 7/2010 | Homan et al. | |
| 2010/0179522 | A1 * | 7/2010 | Companion | A61B 8/085 606/10 |
| 2010/0256614 | A1 * | 10/2010 | Donitzky | A61F 9/008 606/4 |
| 2010/0312095 | A1 | 12/2010 | Jenkins et al. | |
| 2011/0144491 | A1 * | 6/2011 | Sliwa | A61B 5/6885 600/463 |
| 2011/0238060 | A1 | 9/2011 | Lee, Jr. et al. | |
| 2012/0053577 | A1 | 3/2012 | Lee et al. | |
| 2012/0101374 | A1 | 4/2012 | Tearney et al. | |
| 2012/0189998 | A1 | 7/2012 | Kruecker et al. | |
| 2012/0316268 | A1 | 12/2012 | Francis | |
| 2013/0051649 | A1 | 2/2013 | Ruijters | |
| 2013/0072784 | A1 | 3/2013 | Velusamy | |
| 2013/0211243 | A1 | 8/2013 | Zhang et al. | |
| 2013/0218024 | A1 | 8/2013 | Boctor et al. | |
| 2013/0231564 | A1 | 9/2013 | Zagorchev et al. | |
| 2013/0287275 | A1 * | 10/2013 | Stiles | G16H 50/50 382/128 |
| 2013/0315440 | A1 * | 11/2013 | Frank | G06T 7/74 382/103 |
| 2013/0317352 | A1 * | 11/2013 | Case | A61B 90/04 382/128 |
| 2013/0317363 | A1 | 11/2013 | Case et al. | |
| 2014/0058387 | A1 * | 2/2014 | Kruecker | G16H 50/50 606/41 |
| 2014/0064449 | A1 * | 3/2014 | Deng | A61B 6/4441 378/62 |
| 2014/0073907 | A1 * | 3/2014 | Kumar | A61B 10/0241 600/407 |
| 2014/0094660 | A1 * | 4/2014 | Tolkowsky | A61B 8/12 600/300 |
| 2014/0142426 | A1 * | 5/2014 | Razzaque | A61B 34/20 600/424 |
| 2014/0180273 | A1 | 6/2014 | Nair | |
| 2014/0201669 | A1 | 7/2014 | Liu et al. | |

(56) References Cited

U.S. PATENT DOCUMENTS

| | | | |
|---|---|---|---|
| 2015/0080705 A1* | 3/2015 | Partanen | A61B 5/7264 |
| | | | 600/411 |
| 2016/0038247 A1 | 2/2016 | Bharadwaj et al. | |
| 2016/0228097 A1 | 8/2016 | Jaffer et al. | |
| 2017/0000581 A1 | 1/2017 | Tokuda et al. | |
| 2017/0035281 A1 | 2/2017 | Takeuchi et al. | |
| 2018/0017778 A1 | 1/2018 | Ikuta et al. | |
| 2018/0055582 A1* | 3/2018 | Krimsky | A61B 34/10 |
| 2018/0120555 A1 | 5/2018 | Ikuta et al. | |
| 2018/0146999 A1* | 5/2018 | Baust | A61M 25/001 |

FOREIGN PATENT DOCUMENTS

| | | | |
|---|---|---|---|
| JP | 2005160553 A | 6/2005 | |
| WO | 2013055707 A1 | 4/2013 | |
| WO | 2015/116939 A1 | 8/2015 | |
| WO | 2015/116951 A2 | 8/2015 | |
| WO | 2017/024145 A1 | 2/2017 | |

OTHER PUBLICATIONS

C Lorenz, et al., "Multi-scale Line Segmentation with Automatic Estimation of Width, Contrast and Tangential Direction in 2D and 3D Medical Images", In: Troccaz J, Grimson E, Mösges R, editors, CVRMed-MRCAS'97, Springer Berlin Heidelberg, Mar. 1997, pp. 233-242.
C. Xu, et al., "Gradient Vector Flow: A New External Force for Snakes", IEEE Proc. Conf. on Comp. Vis. Patt. Recog. (CVPR'97), Los Alamitos: Comp. Soc. Press, Jun. 1997, pp. 66-71.
Nina Amenta, et al., The Power Crust, Unions of Balls, and the Medial Axis Transform, Computational Geometry 19, Mar. 2001 (41 pages in file).
A. Gouze, et al., "Watershed-Driven Active Contours for Moving Object Segmentation", Proceedings of IEEE International Conference on Image Processing (ICIP), Genova, Italie, vol. II, Sep. 2005, pp. 818-821 (4 pages in file).
Rashed Karim, et al., "Automatic Extraction of the Left Atrial Anatomy from MR for Atrial Fibrillation Ablation", Imperial College London Department of Computing, London, United Kingdom; Royal Brompton Hospital, Cardiovascular and Magnetic Resonance Unit, London, United Kingdom, Apr. 2009 (4 pages in file).
Rashed Karim, "Segmentation of the Left Atrium and Pulmonary Veins from Contrast-Enhanced MR Images", Department of Computing Imperial College London, dissertation, Sep. 2009 (241 pages).
J. Louis Hinshaw, MD, et al., "Percutaneous Tumor Ablation Tools: Microwave, Radiofrequency, or Cryoablation—What Should You Use and Why?", RadioGraphics 2014, vol. 34, No. 5, Sep.-Oct. 2014, pp. 1344-1362 (20 pages in file).
NeuWave Medical Intelligent Ablation, NeuWave System Product Brochure, Sep. 2015 (8 pages).
Soichiro Tani, et al., "Three-dimensional quantitative assessment of ablation margins based on registration of pre- and post-procedural MRI and distance map", Int J Cars, published on Apr. 2, 2016 (10 pages in file).
Imactis, CT Navigation, screenshots obtained at http://www.imactis.com/index.php?module=produit&language=en_EN&PHPSESSID=0cb60af4f54bea83094d4d982ad003a7, screenshots dated Sep. 5, 2019 (2 pages in file) and previously viewed website via listed link on or around Jan. 19, 2017.
Civco, "RAD-Guide Needle Guide for CT & Fluoroscopy", screenshots obtained at http://www.civco.com/mmi/ultrasound/computed-tomography/needle-guide/radguide-610-1187.htm, http://www.civco.com/mmi/Off_Nav/RAD-GUIDE-video.htm, screenshots dated Sep. 5, 2019 (2 pages in file) and previously viewed website via listed link on or around Jan. 19, 2017.
International Search Report and Written Opinion for PCT/US2018/020752, dated May 24, 2018.
International Preliminary Report on Patentability for PCT/US2018/020752, dated Sep. 24, 2019, and Written Opinion of the ISA for PCT/US2018/020752, dated May 24, 2018.

* cited by examiner

METHODS, APPARATUSES AND STORAGE MEDIUMS FOR ABLATION PLANNING AND PERFORMANCE

CROSS-REFERENCE TO RELATED APPLICATION(S)

This application relates, and claims priority, to U.S. Patent Application Ser. No. 62/474,265, filed Mar. 21, 2017, the entire disclosure of which is incorporated by reference herein in its entirety.

FIELD OF THE INVENTION

The present disclosure relates generally to the field of optical imaging and more particularly to ablation planning and ablation performing apparatuses, systems, methods and storage mediums for use with same. Examples of ablation planning and performance applications include imaging, evaluating and characterizing/identifying biological objects or tissue, such as, but not limited to, for identification, location and treatment of lesions/tumors, operation/procedure planning, simulation and ablation performance.

BACKGROUND OF THE INVENTION

There are various forms of ablation, and successful ablation requires good planning. Ablation is normally ordered after diagnosis by oncologists who decide the ablation procedure is the best to treat a lesion/tumor. An interventional radiologist (IR) may be involved to gather and analyze images to accurately characterize tumors and their size and to review results from a biopsy procedure. However, diagnostic imaging is rarely good enough to plan with, so an IR may conduct initial imaging before developing/finalizing an action plan and starting an ablation procedure. The ablation strategy may include selection of an imaging modality in the procedure, probe insertion points, a number of probes and trajectories of the insertion, a modality of ablation such as microwave, cryo, etc., patient position during the procedure, coordinating with other clinicians (e.g., anesthetist, nurses, equipment technicians, etc.), etc.

Ablation takes a lot of planning, and there are a lot of variables. For example, clinicians in ablation planning try to figure out where is the target zone including a lesion/tumor, where are the critical structures/features that must be avoided during procedure, where is the target point in the target zone, what is the entry point on the body surface so that the probe can get into the body and reach a target point(s), what is the trajectory to connect an entry point to a target point while avoiding any critical structure/feature with consideration of needle orientation when scanning the body with the needle inserted, how many probes are needed to form an ablation zone, how big and what shape the ablation zone is, etc. When a lesion/tumor is identified and an ablation zone is defined, based on ablation probe type and quantities, clinicians normally use a visual overlay of the two zones to estimate the coverage zone, which tends to be inaccurate or be a less objective measure since it is a visual estimate.

Even though ablation procedure is very complex, the procedure that is currently performed by clinicians is predominantly done manually and iteratively, which may introduce room for error(s) and may increase the time required to perform ablation (i.e., be inefficient). Planning in particular is largely performed by clinicians with some help from visualization software. Clinicians typically start with reading Computed Tomography (CT) or Magnetic Resonance Imaging (MRI) scans, identify the target region and plan the insertion point and/or trajectory/orientation. For example, in at least one ablation planning scenario, clinicians load Digital Imaging and Communications in Medicine (DICOM) images of a patient into a computer and view slice by slice of the CT or MRI scans of the patient. By going through the DICOM image slices, a clinician may construct a 3D model of internal anatomy of concern. By using the DICOM images, the clinicians may identify where the lesion/tumor is and may identify the relationship of the lesion/tumor and its surrounding critical structure, which clinicians should know well to figure out the probe entry point, target point and consequently the trajectory from the entry point to the target point.

Then the clinicians may identify the entry point on the surface of the body that corresponds to what the clinicians envisioned in the image scans. The clinicians may perform a test drive to insert a needle a little bit, perform a scan, and find the difference between the actual needle insertion demonstrated by the scan and what was expected before the insertion. This gives the clinicians a chance to make any correction and change if necessary. This step may be repeated several times for the needle to reach the target point.

Typically, a target point is in a center of the lesion/tumor. Clinicians may use a pointing device such as a mouse or touch point to mark a location in the center of the lesion/tumor which is shown in the visualization software. Clinicians may either place a probe tip to allow ablation to occur, or may implant seeds for radio/chemo therapy. Even the marking process is manual and approximate in nature. In 3D, marking a center position for an object may not be hard, even though many times it may not be accurate due to human visual and motor action inaccuracy/error. However, a clinician using 3D slice view to figure out a center of a 3D volume which includes a stack of 3D slicers may be difficult and error prone if the center of the volume is the target point, and the clinician may be tricked by image artifacts and/or human limitation in 3D reasoning. In 3D, marking a center position is much harder because of the intricate limitation of visualization/rendering software. Relying on clinicians' intuition, experience and visual understanding to define a target point is not optimal (for reliability, repeatability, traceability, etc.), particularly in 3D space. When the lesion/tumor has a very complicated shape, defining an appropriate target is more or less an art, and it is difficult to achieve consistency.

If multiple needles are needed to make the ablation zone large enough to cover the target zone, clinicians typically use a first needle as reference, and plan the next needles based on the result from the first or previous needle insertion and/or ablation. If there are multiple needle insertions needed, cases are done mostly in an incremental fashion—for example, plan, insert a needle, scan, make an adjustment or modification to the original plan (if needed) based on the scan of the inserted needle, insert another needle, etc.

As discussed above, the common practice of ablation planning is iterative and interactive, and there are many variables to consider such that it is difficult to automate the entire ablation procedure. By way of another major task in ablation, clinicians may desire confirmation of the ablation result. Right now, clinicians typically make or obtain a scan after the ablation is performed in order to see what happens or is happening after the ablation. Clinicians may tend to rely on contrast/intensity changes (e.g., adjustment of visualization software) of the affected area in the images to infer whether the ablation procedure went as planned. If these images do not reveal enough detail(s), clinicians may have to inject a contrast agent into a patient's body to obtain contrast-enhanced images. This additional step only increases the procedures complexity, cost and time.

In various instances, human intervention and adjustment must be done during the procedure. Tools that currently exist to help clinicians in ablation planning are not adequate. For example, visualization software provides clinicians with drawing tools to allow clinicians to define an entry point, a target point and a path, as well as with basic measuring/gauging tool(s). A mechanism of automatically calculating ablation zones based on time and power settings of an ablation device is also available from ablation probe manufacturers. However these mechanisms and tools do not alleviate clinicians from crucial steps in planning such as, but not limited to, defining targets, defining target zone(s), and confirming coverage. Current tools are not integrated with all necessary or preferred components/features for ablation planning and performance, which makes the clinicians still rely on their experience and intuition. Such reliance inevitably results in inconsistency and guess work, or other inefficiencies, such as, but not limited to, longer procedure times, additional steps, less effective or optimal ablation results, etc.

Prior/current methods related to ablation planning assume no occurrence of organ movement and deformation, either implicitly or explicitly. Clinicians employ incremental insertion movement by trial and error to deal with the inevitable organ movement and deformation (e.g., as aforementioned, a clinician may insert a needle a little, scan, read the image(s) to find out how much the needle is off, adjust or change the needle trajectory if needed or keep going, if the target point is moved during probe insertion, etc.). Currently, a first probe insertion is made and scanned to use the scan as a reference. Then subsequent incremental insertions of the probe may be made towards the target with scans after each insertion to assess same. Such a process may include repositioning the patient if needed to make insertion more controllable. Additionally, an IR or clinician may assume the probe is rigid and that organs have no deformation and movement from now until the insertion. Alternatively to scanning, an ultrasound probe along with the ablation probe may be used to guide the probe into the planning direction to reach the target, which requires ultrasound image fusion with CT/MRI (CT fluoroscopy is another technique that may be used with CT during planning and performance of ablation). This not only increases the procedure time, but also wastes a lot of efforts in adjustment/making changes. Of course, it is also likely having impact(s) on or causing possible damage to nearby structure and tissues. Considering organ movement and deformation may make ablation planning and performance more complex, and may hamper interaction between clinicians and ablation planning and performance devices. The reality is that many factors (e.g., breathing, body movement or pose change, organ deformation due to interaction with the probe, etc.) affect probe insertion and may change between planned insertion and actual insertion. Such changes may also invalidate the planned insertion. Respiratory gating, or asking patients to hold their breath, are time consuming monitoring techniques that may be used to assist with insertion. Modeling organ deformation is another way to try to anticipate movement and deformation issues with insertion. However, such procedures do not guarantee success or efficiency.

Ultimately, the purpose of probe insertion is to perform or conduct ablation. It is useful to know how the ablation zone is defined, including whether to use one or more probes to define same and perform ablation. The activities in this stage give a prediction of coverage of ablation over the tumor/lesion, an estimate of overall impact of the ablation zone on the nearby structure, in particular on a critical structure and thermal sinks that must be avoided. Typically, clinicians need to review scans, identify the target and region of a tumor/lesion, and overlay the ablation zone based on a manufacturer's specifications of an ablation probe over the target and region of the tumor/lesion. The effect of the ablation zone on a tumor/lesion region ultimately determines the need to accept, update or reject probe insertion.

Once the probe is setup properly, ablation is thereafter performed. A size and shape of an ablation zone may be closely related to ablation parameters (e.g., temperature, time of ablation device(s), power level, probe type, balloon shape, ball/ellipsoid shape/size, etc.) of an ablation device, and such parameters are typically available from a manufacturer of an ablation device. During ablation, the patient may be monitored and feedback may be received from scans and any other monitoring device(s). A final scanning is performed normally to complete the ablation and to confirm the outcome of the procedure. The IR or other clinician may compare pre and post scans to determine adequate ablation zone/margins, and to confirm whether the target is eliminated via the ablation. Additionally or alternatively, thermal effect or temperature of the tumor area under ablation may be monitored as or as part of the confirmation step. While technologies exist to measure the thermal effect, such technologies do not prove reliable, for example, thermal confirmation is very time sensitive and a measurement may be dramatically different during and after ablation. After ablation completes (e.g., after a preset time), the probe is removed, and clean-up is performed (e.g., applying a bandage to the patient at the insertion point if no more insertion is needed). Waste from the procedure is typically disposed of, sterile drapes are removed, anesthesia is stopped, a patient is rolled out of the room, the room is cleaned, the ablation equipment is unplugged and moved to storage, etc.

In view of the above, there is a need for software, and hardware in some extent, to provide clinicians with help to make ablation easier, more efficient (e.g., reduce procedure time) and more effective (including, but not limited to, more cost-effective (cheaper), optimized for lesion/tumor removal, etc.), in addition to providing enhancement in visualization. There is also a need to present quick information to clinicians after ablation is finished to evaluate the ablation results. There is also a need for a reliable and simple ablation planning and performance apparatus, method and storage medium that takes organ deformation and movement into account, and that provides a better, faster and more objective way to measure and define a target zone, an ablation zone and the overlapping coverage zone.

SUMMARY OF THE INVENTION

Accordingly, it is a broad object of the present disclosure to provide ablation apparatuses and systems, and methods and storage mediums that operate to reduce ablation procedure time through effective planning and performance.

In accordance with one or more embodiments of the present disclosure, ablation planning and performance apparatuses and systems, and methods and storage mediums may operate to identify target tissue type in addition to providing a morphological image to help an operator's diagnostic/planning or ablation performance decision based on tissue information. On or more embodiments of an ablation planning and performance apparatuses and systems, and methods and storage mediums may include or permit at least one of: simulation of a probe path (including planning the path of the probe with real time simulation of respiratory gating and organ motion and deformation), interaction of a probe and target and surrounding organs, clear definition of a position (e.g., an angle) of a patient (such as with real time gravity simulation), clear communication with an interventional (IR) team, tracking of tools used for better inventory and regulatory control, definition of a number and trajectory of probes based on a patient-specific model (e.g., a 3D model, a CT or MRI scan-derived model, etc.), definition of an ablation geometric zone and equipment setting(s) with real time ablation zone simulation, ability to allow planning viewed and archived in real time (e.g., locally, remotely, etc.) for receiving insight from other clinicians, determination of the treatment target that the probe should reach to and estimation of the ablation zone that covers the target, etc.

The effective communication in the planning stage and/or the performance stage may permit the IR to connect with multiple stakeholders from a single source. The software equipped with these features will support the IR in the setup of the operating room (OR) environment and will support the communication with the interventional (IR) team more effectively. On a separate channel, the patient may be updated on the schedule and assisted in preparation for the ablation procedure.

One or more embodiments of the ablation planning and performance apparatuses and systems, and methods and storage mediums may operate to accommodate and adjust for organ movement and deformation.

One or more embodiments of the ablation planning and performance apparatuses and systems, and methods and storage mediums may operate to reduce the number of iterations for the determination of the insertion point(s) and trajectory of the probe after being inserted into the entry point(s). This is beneficial for reducing exposure to radiation when dealing with CT scans and reduces the total time of scanning when dealing with any type of scan, including, but not limited to, CT, MRI or otherwise. In one or more embodiments, registration fiducial markers (such as a sticker grid) may be used on the patient at or near an insertion point before conducting a CT/MRI scan. This registration step helps to accurately correlate physical dimensions to what to see in the scanned images.

One or more embodiments of the ablation planning and performance apparatuses and systems, and methods and storage mediums may operate to improve the determination of the needle or probe trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the ablation plan and better accuracy in positioning a probe. The tracking and guidance system not only tracks the probe position and orientation, but also provides cues for visualization software with the patient's lesion and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

One or more embodiments achieve the above benefits by employing a new approach to the ablation process. Specifically, a medial axis of a 3D object, such as a lesion/tumor (preferably after being segmented), is found, and then target points are picked up along the medial axis. A medial axis is the curve that confines the target point. Once the medial axis is found, it is much easier to define target points along the medial axis, since the medial axis is the "center" of the object in 3D space. Instead of searching target points in the 3D space, it is much easier and consistent to define target points along the medial axis. The number of target points and exact location of target points may then be determined based on information regarding formation of the ablation zone as a result of the application power and time of the ablation probe. Defining ablation zone becomes much simpler and straightforward. As a consequence, optimizing or improving the ablation becomes possible (e.g., a minimal number of needles with a maximal coverage of ablation over the tumor/lesion may be achieved in one or more embodiments). This method reduces the guess work of choosing a target by confining the selection to and at the medial axis, which reduces a search in 3D space down to a search in line(s). This method may be easily implemented and integrated with existing workflow, and is very intuitive. The method also may greatly enhance the accuracy and repeatability of placement of targets in the ablation process or other fields (for example, snake robot navigation/planning in arteries, endoscopic device navigation/planning, colonoscopy probe insertion, etc.). Moreover, this process measures the length of an object, such as the target. The most widely used measures of objects are volume (3D) and area (3D). However, for comparison and assessment of very complicated shapes, volumes and areas may not be appropriate or accurate. Using the medial axis as aforementioned is an accurate way to compare and assess such shapes.

After defining the medial axis and the region of interest thereof, the medical image, medial line and the border line of the determined region of interest may be displayed (e.g., superimposed). A target position may be designated in the displayed image, at which a tip of an ablation device is to be positioned, in response to receiving a user input for selecting a position in the displayed medical image.

Additionally, in one or more embodiments, a security check may be included to perform the check in the surgical room prior to the ablation procedure to ensure maximal security and safety. To make the security check convenient for clinicians (who have scrubbed in and are wearing gloves at that point and may not be able to use their hands for performing the security check), iris and/or face recognition may be incorporated. Once logged in, clinicians may be able to access patient data and communication with peers.

One or more embodiments may include confirmation with margin view as discussed herein below. While quantitative measure of coverage is useful, a visual quick assessment is also very useful in one or more applications. The margin view gives a better view than the common overlay of before and after ablation images to more easily and effectively determine the success of the ablation process.

In one or more embodiments, other imaging technology or endoscope features may be incorporated, such as those disclosed in U.S. Non-Provisional patent application Ser. No. 15/418,329 filed Jan. 27, 2017, which is incorporated by reference herein in its entirety.

In accordance with one or more embodiments of the present disclosure, ablation planning and performance apparatuses and systems, and methods and storage mediums may operate to characterize biological objects, such as, but not limited to, lesions, tumors, critical structures, etc.

In accordance with at least another aspect of the present disclosure, the ablation planning and performance technique(s) discussed herein may be employed to reduce the cost of at least one of manufacture and maintenance of ablation planning and performance devices, systems and storage mediums by reducing or minimizing a number of components therein to cut down cost.

According to other aspects of the present disclosure, one or more additional devices, one or more systems, one or more methods and one or more storage mediums for ablation planning and performance are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, systems, methods and storage mediums for performing ablation planning and/or performance are disclosed herein. In accordance with at least one aspect of the present disclosure, one or more devices, systems, methods and storage mediums discussed herein perform ablation planning and/or ablation performance using at least one of the following methods: security or credential checking, integrating several steps (e.g., segmentation, registration, differential image view, etc.) to enhance an experience of a user when iteratively and interactively exploring and evaluating the planning and/or performance process, determining a medial axis of a target and performing confirmation with margin view. In one or more embodiments, these methods may be combined to further enhance the effectiveness in planning and ablation performing procedure. Several embodiments of the methods, which may be carried out by the one or more embodiments of an apparatus, system and computer-readable storage medium of the present disclosure are described diagrammatically and visually in FIGS. 1 through 15.

Figure 1:
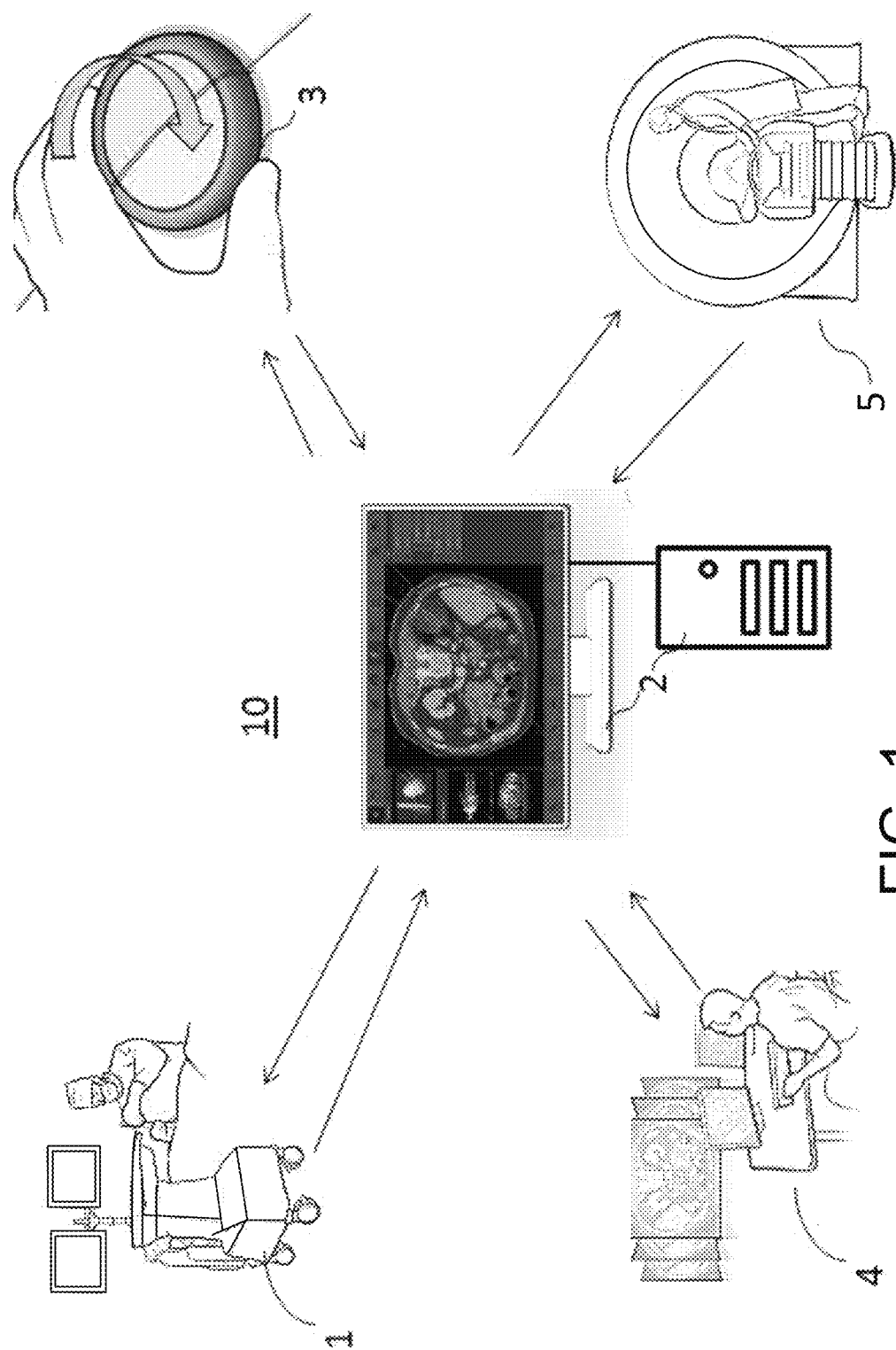
FIG. 1 is a schematic diagram showing an embodiment of a system for performing ablation planning and/or ablation in accordance with one or more aspects of the present disclosure.
Figure 2:
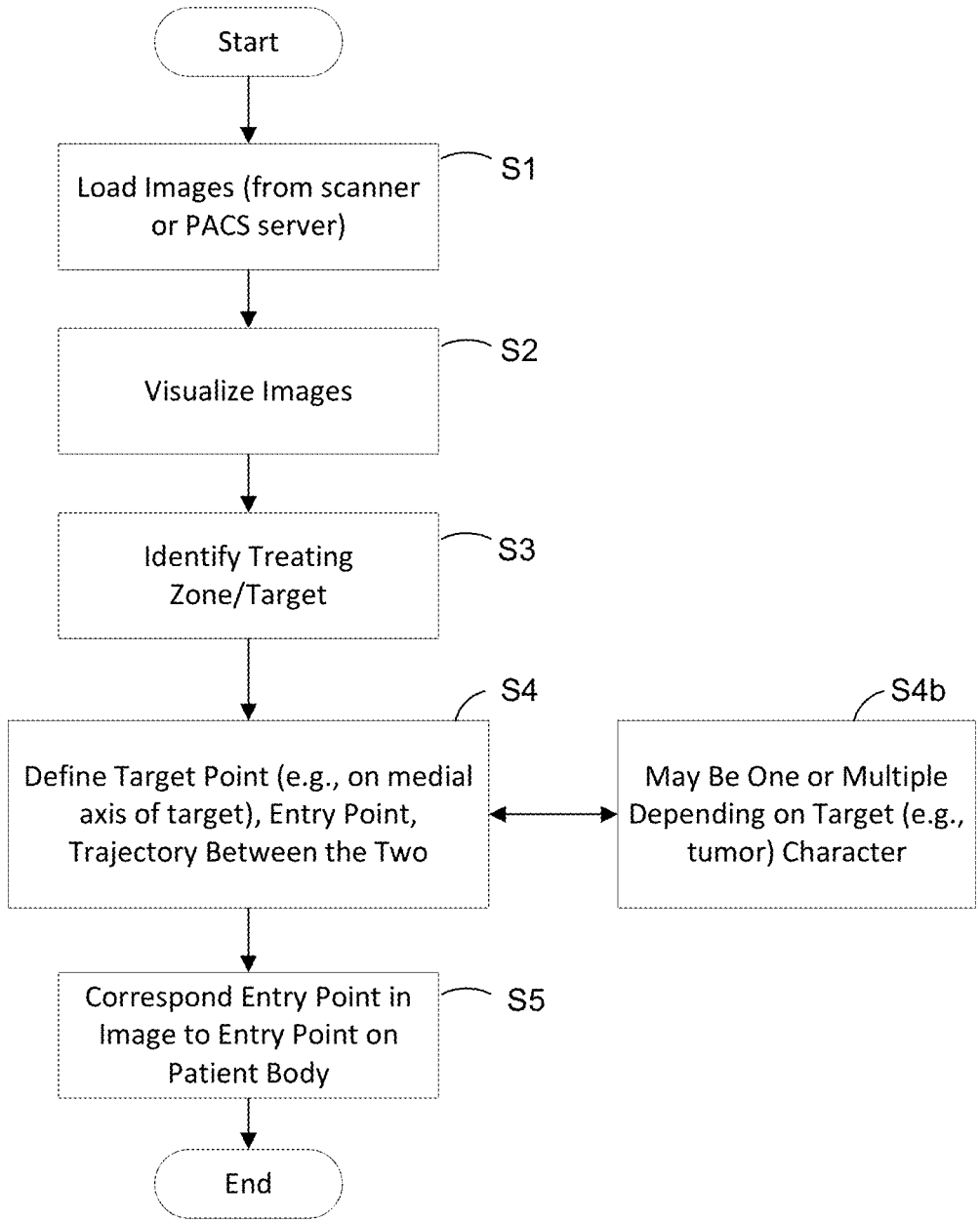
FIG. 2 is a flow chart showing at least one embodiment of a method for performing ablation planning and/or ablation in accordance with one or more aspects of the present disclosure.
Figure 3:
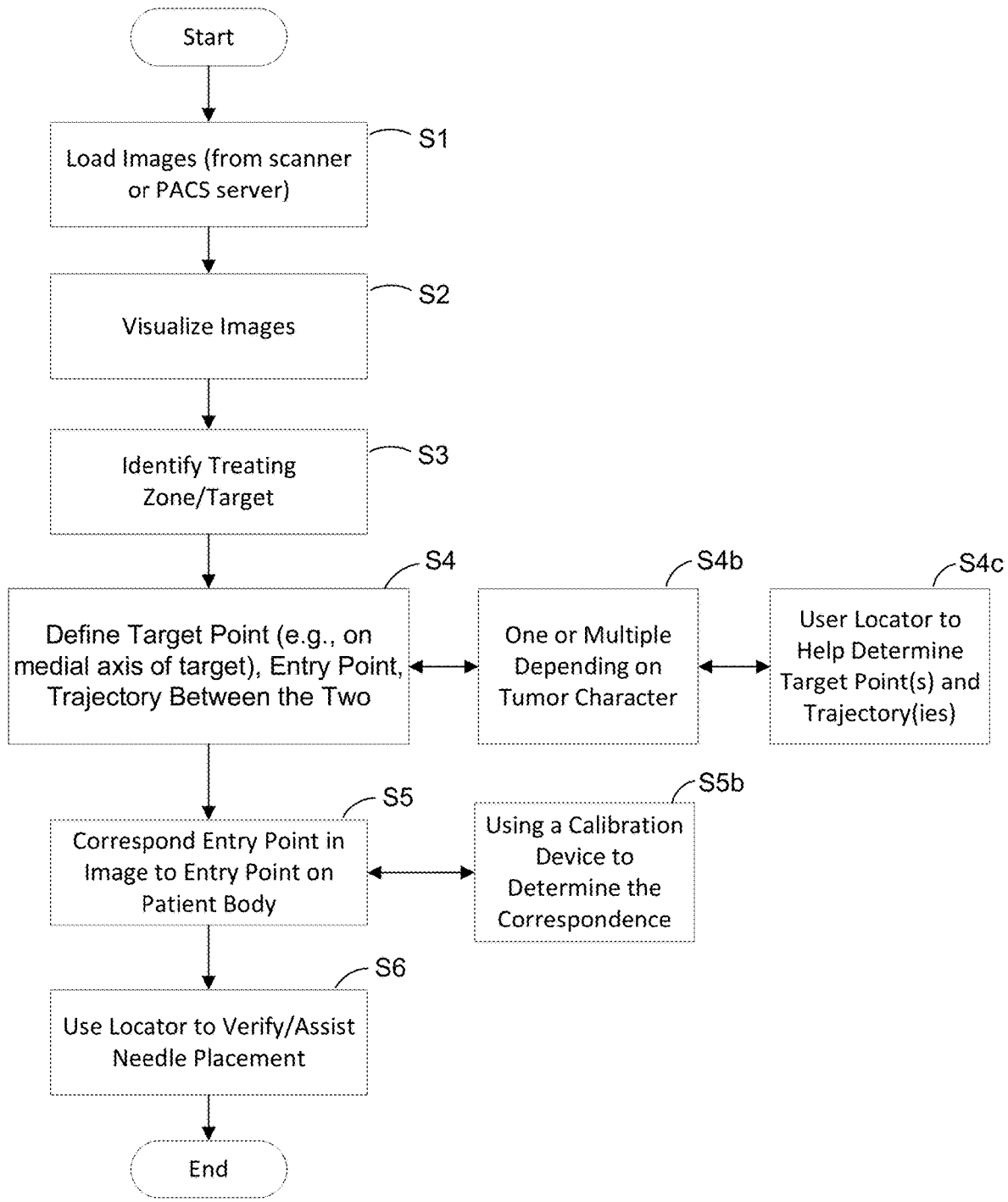
FIG. 3 is a flow chart showing at least another embodiment of a method for performing ablation planning and/or ablation in accordance with one or more aspects of the present disclosure.
Figure 4:
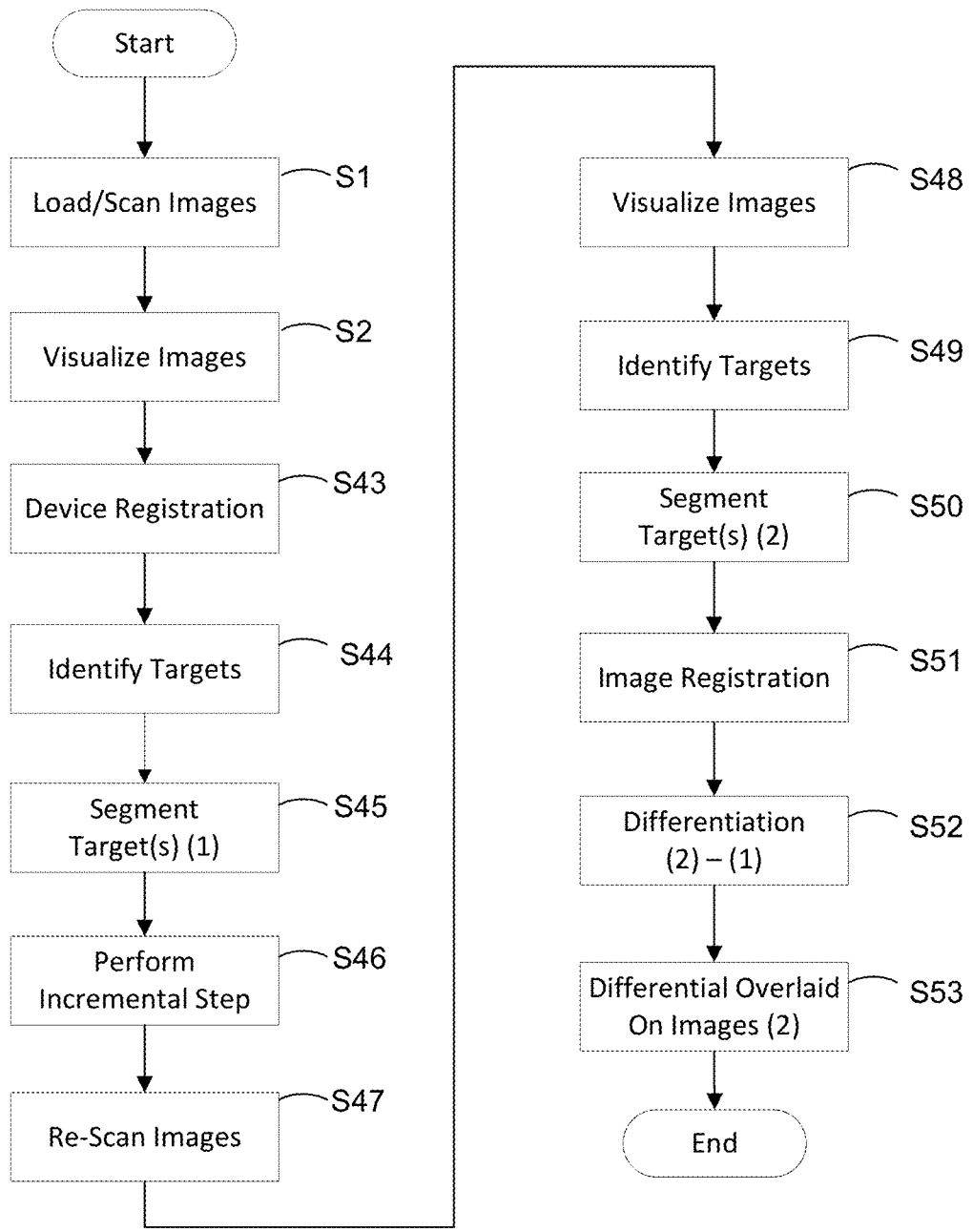
FIG. 4 is a flow chart showing at least a further embodiment of a method for performing ablation planning and/or ablation in accordance with one or more aspects of the present disclosure.

In accordance with at least one aspect of the present disclosure and as aforementioned, one or more methods for performing ablation planning and/or ablation performance are provided herein. At least FIGS. 2-3 illustrate flow charts of at least one respective embodiment of a method for performing ablation planning and/or ablation performance using an ablation device, system (e.g., such as a system 10 as shown in FIG. 1) or storage medium. At least one embodiment of a system 10 may include an ablation device 1, an ablation planning computing system (which may include software and/or hardware for implementing the ablation planning and/or performance) or computer 2 (alternative embodiment of a computer 2' that may be used is discussed herein below), a locator device (such as, but not limited to, an image-plane localizer) 3, a Picture Archiving and communication system (PACS) 4 and an image scanner 5 (such as, but not limited to, a CT scanner, MRI device or other scanning apparatus). As shown diagrammatically in FIG. 1, the ablation planning methods of the present disclosure may be involved with all major aspects of ablation planning and performance. For example, the system 2 may communicate with the image scanner 5 to request information for use in the ablation planning and/or performance, such as, but not limited to, bed or slice positions, and the image scanner 5 may send the requested information along with the images to the system 2 once a clinician uses the image scanner 5 to obtain the information via scans of the patient. By way of another example, the system 2 may communicate and be used with a locator device 3 (such as an image-plane localizer that may be a patient-mount device and may be rotated as shown to help locate to biological object, such as a lesion or tumor) to obtain information from the patient when conducting ablation planning and/or ablation performance. The system 2 may further communicate with a PACS 4 to send and receive images of a patient to facilitate and aid in the ablation planning and/or performance. Once the plan is formed, a clinician may use the system 2 along with an ablation device 1 to consult an ablation chart or plan to understand the shape and/or size of the targeted biological object to be ablated. Each of the ablation device 1, the system 2, the locator device 3, the PACS 4 and the scanning device 5 may communicate in any way known to those skilled in the art, including, but not limited to, directly (via a communication network) or indirectly (via one or more of the other devices 1, 3 or 5; via one or more of the PACS 4 and the system 2; via clinician interaction; etc.).

One or more embodiments of the ablation planning and performance apparatuses and systems, and methods and storage mediums may operate to improve the determination of the needle or probe trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the ablation plan and better accuracy in positioning a probe. The tracking and guidance system not only tracks the probe position and orientation, but also provides cues for visualization software with the patient's lesion and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

Preferably, the method(s) may include one or more of the aforementioned ablation planning and performance steps, including, but not limited to, one or more of the following: (i) loading images (e.g., from a scanner, a PACS or other scanning device/system, or using a fresh or newly scanned image) (see step S1 in FIG. 2); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by moving at least one line (e.g., an axis or axes) to cut through one or more planes to reformat a 3D data set and display the reformatted slices in the 3D view; etc.)) (see step S2 in FIG. 2); (iii) identifying a treating zone or target (e.g., a lesion or tumor) (see step S3 in FIG. 2); (iv) defining a target point, an entry point and a trajectory between the target and entry points (see step S4 in FIG. 2) (as shown in step 54*b*, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 2). Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). In one or more embodiments of the present disclosure, a method is provided to determine or suggest a target point or points that is clinically the best choice (e.g., mathematically, statistically, etc.) for placement of the target point(s). In one or more embodiments, target point(s) may be determined by finding or determining a medial axis or center line of the target or treating zone (see step S4 of FIG. 2).

For any identification of a target or targets step(s) discussed herein (such as, but not limited to, step S3 of FIGS. 2-3; step S44 of FIG. 4; etc.), any method of identifying a target biological object or zone, including those known to those skilled in the art, such as a clinician, and including the additional method(s) provided herein, may be employed. For example, in one or more embodiments, a target zone and target points are to be identified. A target zone may be identified by an image segmentation method(s). Clinicians may initially define a few points, called seeds, which may or may not be the target points within an identified a target region, such as a lesion or tumor region. In one or more embodiments, an active contour model, such as a snake algorithm (see e.g., one example explained by C. Xu and J. L. Prince in "Gradient Vector Flow: A New External Force for Snakes", Proc. IEEE Conf. on Comp. Vis. Patt. Recog. (CVPR), Los Alamitos: Comp. Soc. Press, pp. 66-71, June 1997), may be used to iteratively determine a boundary of the target region. The initial seeds may not converge to a true boundary quickly, so, in one or more embodiments, a watershed method (see e.g., one example explained by Gouze A., De Roover C., Herbulot A., Debreuve E., Barlaud M., Macq B. in "Watershed-driven Active Contours for Moving Object Segmentation", in Proceedings of IEEE International Conference on Image Processing (ICIP), vol. II, pp 818-821, Genova, Italie, September 2005) may be used together with the snake algorithm to make the segmentation smoother and faster. Compared to manually drawing a boundary of a target region, such as a lesion or tumor region, such a method or methods generate a far more accurate and consistent boundary, which may be used to determine a volume of a target (e.g., a tumor or lesion) and may be used in a later stage for quantitatively characterizing the tumor or lesion and assessing ablation results. The resulting boundary forms a target zone.

Additionally or alternatively, one or more method(s) of the present disclosure may further include performing ablation planning and/or performance with a locator device as shown in FIG. 3. In addition to the steps shown in FIG. 2 (the details of which are aforementioned and will not be repeated herein accordingly), such one or more method(s) employing a locator device, such as the locator device 3 may further include, but are not limited to, one or more of the following: (i) using a locator, such as the locator device 3, to help determine the target point(s) and trajectory(ies) in steps S4 and/or S4b (see steps S4, S4b and S4c in FIG. 3); (ii) using a calibration device (e.g., such as, but not limited to, fiducial markers, systems and methods of registration, such as those disclosed in U.S. patent application Ser. No. 14/755,654 and published in U.S. Pat. Pub. No. 2017/0000581, which are incorporated by reference herein in their entireties) to determine or assist with the correspondence step of S5 (see steps S5 and S5b in FIG. 3); and (iii) using a locator, such as the locator device 3, to verify and/or assist with needle placement when performing ablation for the patient (see step S6 in FIG. 3). In one or more embodiments of the present disclosure, at least one embodiment of a method for performing ablation planning or ablation performance is to use such calibration device(s) and/or locator device(s) to increase or maximize the success of the ablation procedure depending on one or more variables, such as, but not limited to, needs of the patient, characteristics of the lesion/tumor, if movement of the patient is needed during the procedure, etc. In one or more embodiments of the present disclosure, such calibration device(s) and/or locator device(s) assist a clinician in finding a medial axis or center line of the target biological object, such as a lesion or tumor.

In one or more embodiments, workflow for a particular procedure, such as ablation planning and/or ablation performance, may be combined with segmentation, registration and differential image view steps to provide better differential images (see e.g., FIG. 4 and related discussion below), which avoid the generation of misleading artifacts in images and/or avoid other issues with procedure-related problems. Differential images are a quick way to give clinicians feedback of ablation results. While thermal maps may be used in one or more embodiments, such thermal maps may be affected by environmental changes, such as blood flow, and measurements may not be easily localized depending on the circumstances. Various types of ablation may be used in one or more embodiments (e.g., cryoablation, microwave ablation, laser ablation, etc.). While cryoablation may be used, iceballs may form, and are very visible under MRI. Ultrasound may be used in one or more of the methods discussed herein for navigation, and some indication of an ablation result may be obtained from the same tool. However, ultrasound images may be noisy and may be hard to quantitatively measure. Regardless of which detection or monitoring tool/technique is employed, the integration of the workflow with segmentation, registration and differential image view steps reduces and/or avoids such issues to provide a useful differential image or images for clinicians to use in one or more procedures (e.g., ablation, radiotherapy, etc.).

For ablation procedures, one probe ablation or multi-probe ablation may be performed. For multi-probe ablation, serial or parallel multi-probe ablation may be performed. In serial ablation, ablation is done in sequence of one probe being inserted, ablated, confirmed, then another probe being inserted, ablated, confirmed, and repeating such steps if more probes are needed. In parallel ablation, all probes are inserted before ablation starts. Clinicians may decide which ablation approach is chosen. No matter which approach is chosen, a confirmation stage is needed after the ablation is done. Based on information from each confirmation, a clinician may determine whether additional ablation is needed, and, if so, where to plan for the next probe to be used. Confirmation is also provides clinicians with an indication as to whether the margin is reached or overreached to evaluate the results of the ablation procedure.

To aid clinicians in performing confirmation steps, one or more embodiments of the present disclosure may include confirmation with margin view so that confirmation or any other determination process requiring clear image feedback may be performed more effectively. While quantitative measure of coverage is useful, a visual quick assessment is also very useful in one or more applications. The margin view gives a better view than the common overlay of before and after ablation images to more easily and effectively determine the success of the ablation process. In one or more embodiments, the target(s), such as lesion(s) or tumor(s) may be segmented before and after ablation occurs, and differentiation between the two sets of segmented target images may be determined. Thereafter, the differential may be overlaid on the after-ablation images to evaluate the ablation process. Additionally or alternatively, one or more method(s) of the present disclosure may further include performing ablation planning and/or performance with a locator device as shown in FIG. 3. One or more embodiments of methods for evaluating or determining a margin view may include, but are not limited to, one or more of the following: (i) loading images (e.g., from a scanner, a PACS or other scanning device/system, or using a fresh or newly scanned image) (see step S1 in FIG. 4, which is the same as step S1 in FIG. 2 such that the above details regarding same are not repeated herein); (ii) visualizing images (e.g., such as by showing multiple panes (views) (e.g., each view may represent a different aspect of the image); as described above for step S2 in FIG. 2; as described below for FIGS. 9a-9f (e.g., in medical image software, such as, for example, the application shown in FIGS. 9a-9f); as otherwise described herein; etc.) (see step S2 in FIG. 4, which is the same as step S2 in FIG. 2 such that the above details regarding same are not repeated herein); (iii) performing device registration (also referred to herein as device calibration) to make a correct correspondence or alignment between an image and real world dimensions for a patient (see step S43 of FIG. 4; see also, steps S5-S5b of FIG. 3 which may be incorporated into or used as step S43); (iv) identify a target or target(s), such as a zone or biological object (see step S44 of FIG. 4); (v) segmenting the identified targets (at one reference point in the planning or procedure (e.g., before moving a needle, before performing ablation, before performing the next iterative or incremental planning step (either during the procedure or in simulation or planning), before moving a patient, etc.)—also referred to herein as "targets (i)", i.e., the targets identified at stage (1)) (see step S45 in FIG. 4); (vi) performing an incremental planning or performance step (e.g., move a needle, insert a new probe or needle, perform ablation, perform the next planning step, moving a patient, etc.) (see step S46 in FIG. 4); (vii) re-scanning the targets or obtaining newly scanned images of the targets after performing the incremental planning or performance step (see step S47 in FIG. 4); (viii) visualizing images (e.g., such as by showing multiple panes (views) (e.g., each view may represent a different aspect of the image); as described above for step S2 in FIG. 2; as described below for FIGS. 9a-9f; as otherwise described herein; etc.)) (see step S48 in FIG. 4, which may be the same as or similar to step S2 in FIG. 2 such that the above details regarding same are not repeated herein); (ix) identifying a target or target(s), such as a zone or biological object (see step S44 of FIG. 4, which may be the same as or similar to step S44 of FIG. 4 or to step S3 in FIGS. 2-3 such that the above details regarding same are not repeated herein); (x) segmenting the re-scanned targets (at a second reference point in the planning or procedure (e.g., after moving a needle, after moving or adding a probe, after performing ablation, after performing the next iterative or incremental planning step (either during the procedure or in simulation or planning), etc.)—also referred to herein as "targets (2)", i.e., the targets as re-scanned at stage (2) after stage (1)) (see step S50 of FIG. 4); (xi) performing image registration (e.g., before conducting differentiation of current images and previous images) (see step S51 of FIG. 4); (xii) performing differentiation of current images (e.g., images of stage (2)) and previous images (e.g., images of stage (1)) to enhance the view of the effect of the procedure (e.g., ablation (especially when using microwave or radiofrequency (RF) ablation (in one or more embodiments, differentiation subtraction may not be needed for cryoablation)), radiotherapy, etc.) (see step S52 of FIG. 4); and (xiii) overlaying the differential on the current images (e.g., images of stage (2)) (see step S53 of FIG. 4). Image segmentation and registration may be performed using any method known to those skilled in the art, such as a clinician.

Figure 5:
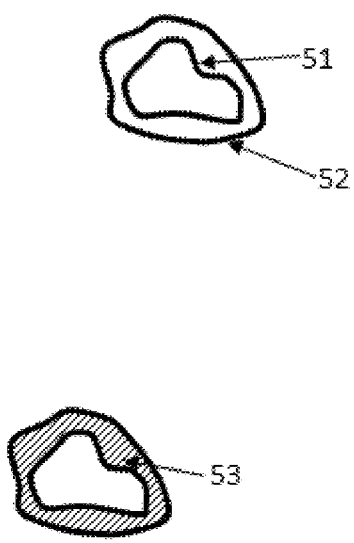
FIG. 5 is a diagram showing an embodiment example of a biological object, such as a lesion or tumor, being displayed with an ablation zone and an image of the biological object having a margin map included in accordance with one or more aspects of the present disclosure.
Figure 6:
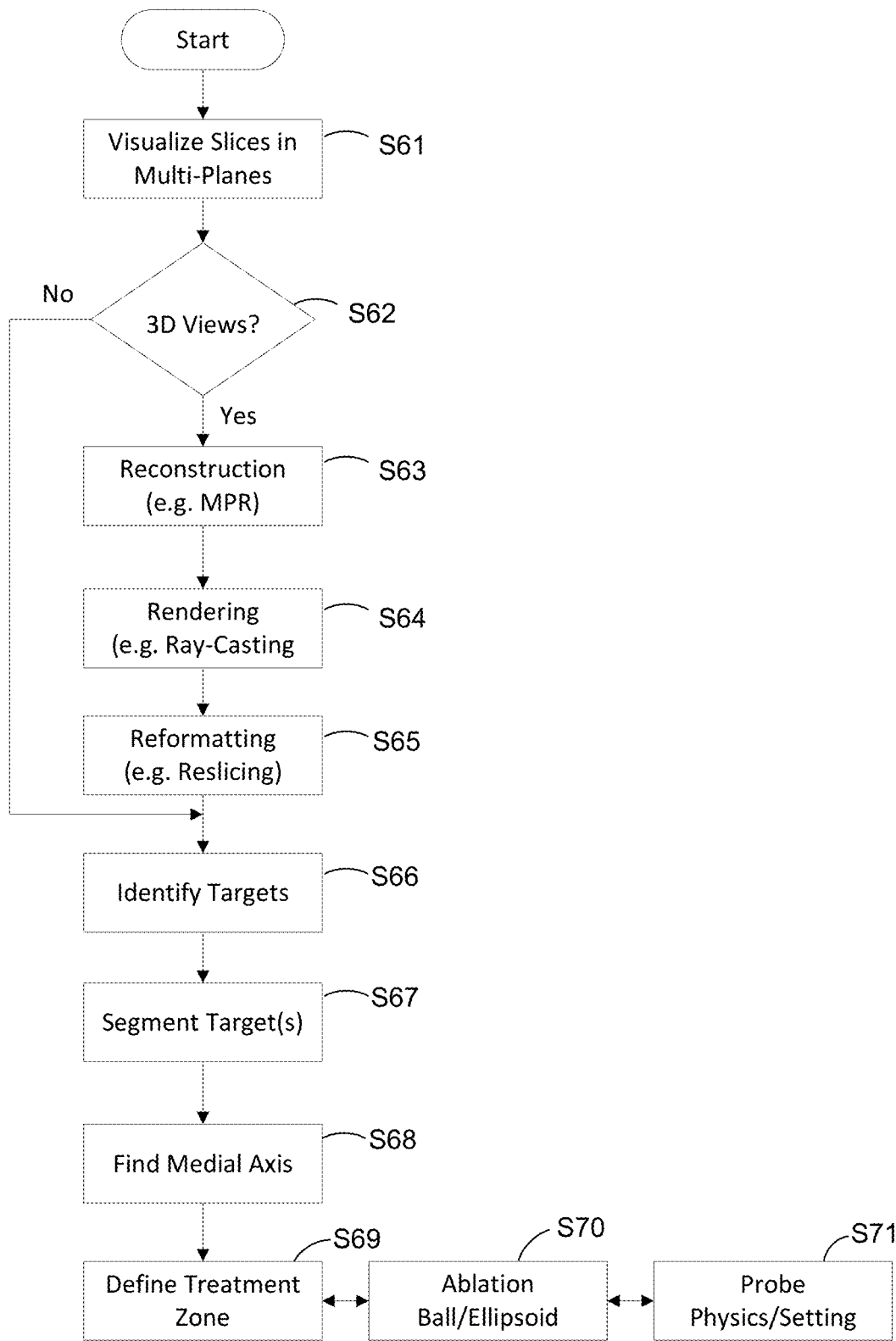
FIG. 6 is a flow chart showing at least another embodiment of a method for performing ablation planning and/or ablation in accordance with one or more aspects of the present disclosure.

The image differentiation may be used to enhance the visualization of an ablation result, monitor probe progression during insertion, or to track any other incremental step in a procedure (e.g., ablation, radiotherapy, etc.). By way of example, a concept of such an enhancement after performing ablation is shown in FIG. 5. The target or target zone 51 of a biological object (such as a lesion or tumor) is surrounded by an ablation zone or ablated zone (once ablation is performed) 52. As such, in one or more embodiments, such as when performing differentiation (e.g., step S52 of FIG. 4) and overlaying the differential on the current image(s) of stage (2) (e.g., step S53 of FIG. 4) or final images, a margin map 53 is formed. The margin map 53 may be used by a clinician to determine whether or not to edit a procedure plan and/or to evaluate whether the plan or procedure is optimal (e.g., the best option available) or has been successful (and to gauge how successful). This improved ability to measure success is good for feedback (such as for the clinician, patient, hospital, other clinicians consulting such results, etc.), and provides an outcome oriented application in one or more embodiments of the present disclosure. For example the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion.

Additionally or alternatively, clinicians may perform simulations with one or more embodiments of the planning methods/software of the present disclosure to create an optical plan, to accommodate one or more variables (e.g., patient movement during the procedure, tissue deformations, etc.), and to evaluate the potential outcome. By way of at least one example, a simulation of an ablation zone (e.g., an ice ball for cryoablation, a balloon for microwave ablation, etc.) may be conducted. By way of another example, a simulation may be performed to mimic tissue deformation. For example, if clinicians segmented an organ or tumor (suppose an oval shape for purposes of the example simulation), the medial axis algorithm may take the segmented object as input and generate a medial axis output (typically it is a curve), which may be overlaid on the segmented object. By dragging and manipulating the medial axis curve, the curve may change its shape and location in space. Due to the fact that a volume may be reconstructed from a medial axis curve, the deformation may be simulated or obtained by dragging and manipulating the medial axis.

One or more embodiments of the ablation planning and performance apparatuses and systems, and methods and storage mediums of the present disclosure may operate to reduce the number of iterations for the determination of the insertion point(s) and trajectory of the probe after being inserted into the entry point(s). This is beneficial for reducing exposure to radiation when dealing with CT scans and reduces the total time of scanning when dealing with any type of scan, including, but not limited to, CT, MRI or otherwise. In one or more embodiments, registration with fiducial markers (such as a sticker grid) may be used on the patient at or near an insertion point before conducting a CT/MRI scan. This registration step helps to accurately correlate physical dimensions to what to see in the scanned images.

After a target zone is identified, clinicians may pick up a point or a few points within the target zone as target point(s). From there on, an ablation zone (for example iceball) may be defined on or around the target zone (e.g., in the case of the iceball example, the ball may be centered on the ablation zone).

While clinicians may pick target points by trial and error, such trial and error leads to inefficiencies, such as, but not limited to, longer procedure time, more invasive and repeated steps (e.g., needle or probe insertion/movement), lack of accuracy, etc.

One or more embodiments achieve the above benefits by employing a new approach to the ablation process, which is to determine a medial axis or center line of a target zone or target biological object, such as, but not limited to, a lesion or tumor. Such objects or target zones may have complicated geometry, so it is useful in one or more embodiments to handle complicated shapes in 3D space. In at least one embodiment, a medial axis or center line of a 3D object, such as a lesion/tumor (preferably after being segmented), is found, and then target points are picked up along the medial axis or center line. A medial axis or center line is the curve or line that confines the target point(s). Once the medial axis is found, it is much easier to define target points along the medial axis, since the medial axis is the "center" of the object in 3D space. Instead of searching target points in the 3D space, it is much easier and consistent to define target points along the medial axis. The number of target points and exact location of target points may then be determined based on information regarding formation of the ablation zone as a result of the application power and time of the ablation probe. Defining ablation zone becomes much simpler and straightforward. As a consequence, optimizing or improving the ablation becomes possible (e.g., a minimal number of needles with a maximal coverage of ablation over the tumor/lesion may be achieved in one or more embodiments). This method reduces the guess work of choosing a target by confining the selection to and at the medial axis, which reduces a search in 3D space down to a search in line(s). This method may be easily implemented and integrated with existing workflow, and is very intuitive. The method also may greatly enhance the accuracy and repeatability of placement of targets in the ablation process or other fields (for example, snake robot navigation/planning in arteries, endoscopic device navigation/planning, colonoscopy probe insertion, etc.). Moreover, this process measures the length of an object, such as the target. The most widely used measures of objects are volume (3D) and area (3D). However, for comparison and assessment of very complicated shapes, volumes and areas may not be appropriate or accurate. Using the medial axis as aforementioned is an accurate way to compare and assess such shapes.

There are many standard references to find a medial axis, such as, for example, an algorithm described in the paper "The power crust, unions of balls, and the medial axis transform by Nina Amenta, Sunghee Choi, and Ravi Krishna Kolluri, Computational Geometry 19 (2001)". The actual C++ implementation can be found in "https://code.google-.com/archive/p/powercrust/".

Figure 7A:
FIG. 7a is a diagram showing an embodiment example of biological objects being displayed with respective medial axes or center lines in accordance with one or more aspects of the present disclosure.
Figure 7B:
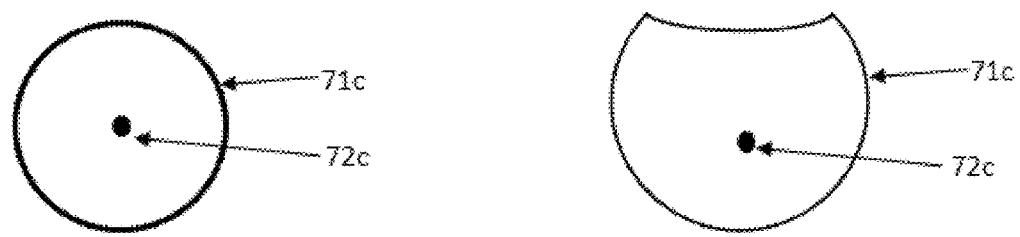
FIG. 7b is a diagram showing an embodiment example of a biological object being displayed with a medial point or center point and illustrating how the medial point or center point may change due to deformation or movement of the object in accordance with one or more aspects of the present disclosure.

One or more embodiments of methods for defining a treatment or target zone or a target that is a biological object using a medial axis may include, but are not limited to, one or more of the following: (i) visualizing slices of images in multi-planes (e.g., such as by showing multiple panes (views) (e.g., each view may represent a different aspect of the image); as discussed above for step S2 in FIG. 2; as discussed for FIGS. 9a-9f; as otherwise described herein; etc.) (see step S61 in FIG. 6); (ii) determining whether the slices of images are 3D views or not (see step S62 in FIG. 6); (iii) if "Yes", performing reconstruction (e.g., via multiplanar reconstruction (MPR)), rendering (e.g., via Raycasting) and reformatting (e.g., via re-slicing) of the images; or if "No", proceeding to step S66 of FIG. 6; (iv) identifying targets (see step S66 of FIG. 6, which is the same or similar to steps S3 of FIGS. 2-3 and steps S44 and S49 of FIG. 4 and will not be re-described herein); (v) segmenting the target zone or zones or the target(s) (see step S67 of FIG. 6, which is the same or similar to step S45 or step S50 of FIG. 4, and will not be re-described herein); (vi) finding, calculating or determining the medial axis or center line of the target zone(s) or target(s) (see step S68 of FIG. 6); and (vii) defining the treatment zone (e.g., an ablation zone or zone to be ablated, a radiotherapy zone, etc.) (see step S68 of FIG. 6). In one or more embodiments, step S68 for defining the treatment zone may further include at least one of the steps of considering the ablation ball/ellipsoid (e.g., size/shape thereof) (see step S70 of FIG. 6); and considering the probe physics or settings (or physics or settings of multiple probes as needed) (see step S71 of FIG. 6). For example, clinicians may define the treatment zone or may define target points along the medial axis or axes while considering, and in order to accommodate, a ball/Ellipsoid shape/size and whether to use a single probe or multiple probes. In one or more embodiments, the method(s) or algorithm(s) discussed herein may determine a medial axis of a volume to obtain the medial axis transform (MAT). A medial axis of a 3D object may be constructed by centers of maximally-inscribed balls inside the object. Therefore, it is logical to use a medial axis to locate the centers of the ablation zone(s), such as iceball (s). As shown in FIG. 7a, medial axes 72a and 72b have been defined and determined for respective target zones 71a and 71b (the left target zone 71a having a larger volume and the right target zone 71b having a larger length relatively to each other).

Another benefit of using a medial axis is that the medial axis may be used to trace the deformation and movement of the object during the ablation. By way of an illustrative example shown in FIG. 7b, a target zone 71c (which has a circular shape) has a medial point 72c located at the middle thereof. After the target zone 71c becomes deformed such that the top portion thereof is depressed (e.g., due to environmental change(s), via patient movement during a procedure, due to needle or probe insertion, etc.), the medial point 72c is located lower in the target zone 71c accordingly. The methods disclosed herein allow clinicians to determine changes in a medial axis or axes or in medial point(s) to appropriately adjust for environmental changes that occur during a procedure (e.g., an ablation, radiotherapy, etc.). The clinician may re-image the zone at predetermined intervals, after a change is detected, or other timing as the clinician finds useful, and the medial axis(es) or point(s) are determined or found using the algorithm(s) or method(s) discussed above.

Figure 8A:
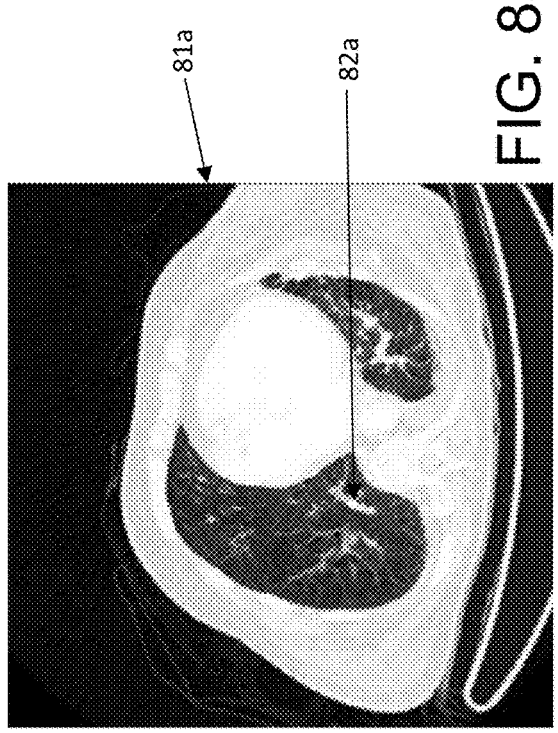
FIGS. 8a-8d are images showing an embodiment of a process to extract a medial axis from a CT scan of an abdomen for an object in accordance with one or more aspects of the present disclosure.
Figure 8B:
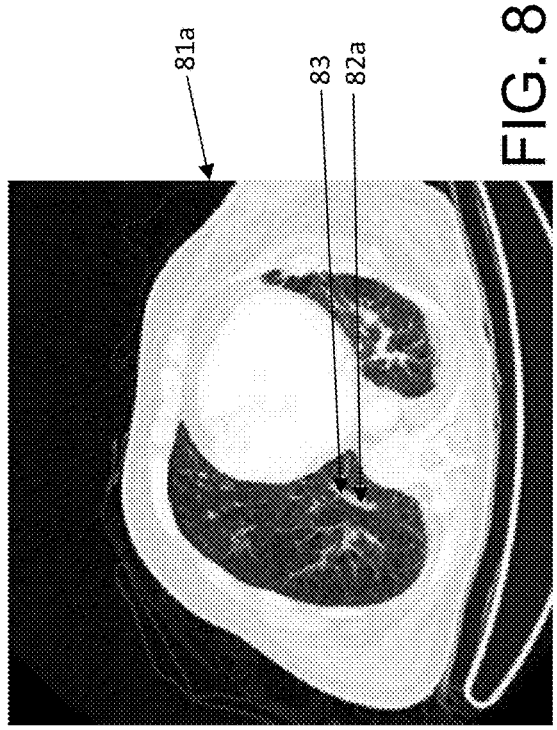
Figure 8C:
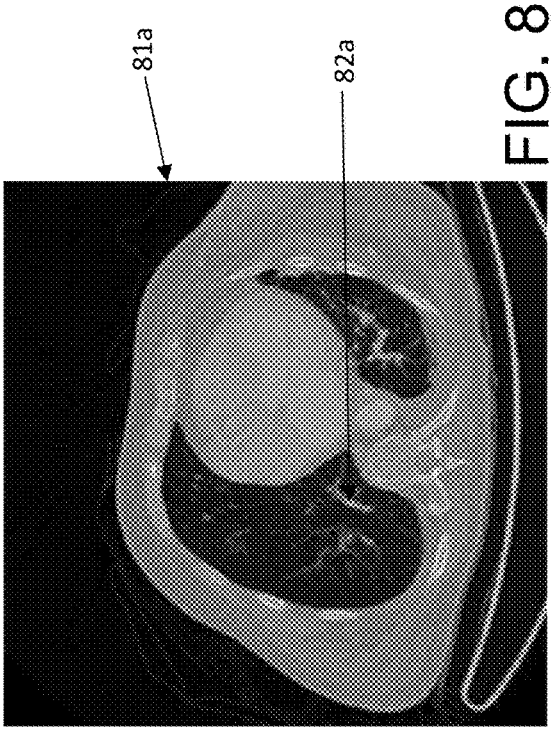
Figure 8D:
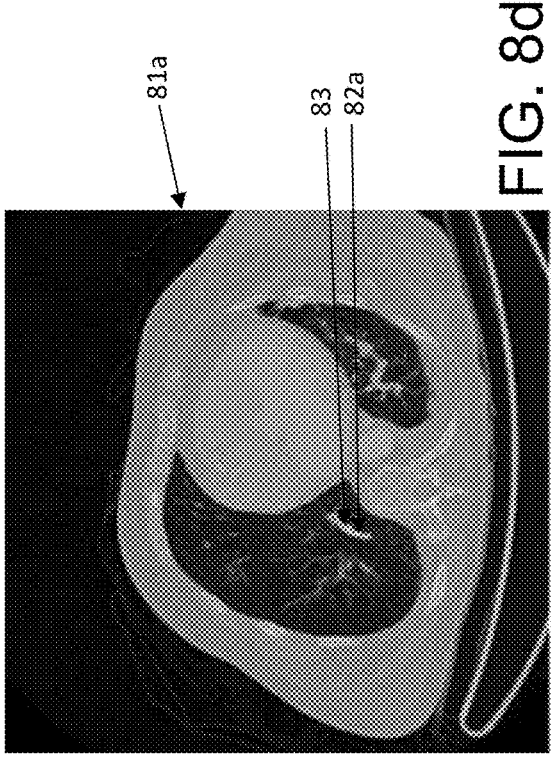

FIGS. 8a-8d show a simplified process to extract a medial axis from a CT scan of an abdomen for an object. FIG. 8a shows an original image of an abdomen CT scan having an image 81a and a target object to be extracted or ablated 82a. FIG. 8b shows initial seeds 83 inside of the object or target zone 81a. In FIG. 8b, the seeds 83 extend along the target object 82a (and, in one or more embodiments, may substantially overlap the target object 82a). Different methods may be used to insert initial seeds, such as the seeds 83, for example, via the aforementioned watershed method. After a predetermined number of iterations (e.g., too iterations as shown in FIG. 8C), an active contour (snake) algorithm converges to the target object 82a to be ablated or extracted from the original image. The dilation process used for FIG. 8C is fast (less than 1 second for too iterations), and clearly shows the segmented object 82a. FIG. 8d shows the medial axis 84 of the segmented object 82a, and also shows the image by blending two images (i.e., the original image and the other being the medial axis extracted from the segmented object). The medial axis approach may also be used to detect organ movement and organ deformation before and after ablation registration. In a typical procedure that requires multiple needle insertions, clinicians do at least one scan after each insertion, to check if the insertion gets to the target as planned, and to plan for the next insertion. In order to correctly insert the subsequent needles, clinicians often estimate the organ movement and deformation in view of the previous needle insertion. This is rarely intuitive and rarely accurate, and is often misleading. In one or more embodiments of the present disclosure, with a medial axis defined for both a target (such as the same organ) segmented in a previous scan and a current scan, clinicians may register the two sets so the target (such as the same organ) may be aligned, and the movement and the deformation may be seen clearly.

Additionally, the medial axis may be used as a reference for clinicians to confirm or deny the accuracy of target point(s) selected by the clinician in the target object. For example, even when clinicians select a point or a few points in the medial axis of a target, the points may not be in the medial axis, due to human errors in vision and motor action. Unless viewed in the right scale of the visualization, the selected points may not be placed in the axis but may still be seen in the line visually. Even though one or more such points may be close to where the clinician intends to place the subject points, the off the target placement may result in inconsistency and error for purposes of planning and conduct a procedure, such as ablation, radiotherapy, etc. A solution provided by one or more embodiments of the present disclosure is to automatically define a ball around the point placed and then find out or determine whether the ball intercepts the medial axis. By way of at least one example, initially, the radii may be set to something like 5 pixels. If there is no intercept occurrence, a process or algorithm (e.g., performed via software and/or hardware) in one or more embodiments of the present disclosure may automatically increase the radii by a predetermined amount (e.g., to 10 pixels), and another search for interception is conducted. If an interception is found, then the method or algorithm (e.g., performed via software and/or hardware) may find the shortest distance of the interception point and the medial axis. The distance can be used to snap the point on to the medial axis, which makes the place target point really on the medial axis. Appendix 9 depicts the process of snapping the user clicked point onto the nearest point in medial axis.

Calculating or determining a medial axis using one or more of the above-described process(es) or algorithm(s) is efficient and fast, so the medial axis may be displayed as soon as the target (e.g., a lesion, a tumor, etc.) is segmented. Displaying the medial axis as soon as the target (e.g., a lesion, a tumor, etc.) is segmented (or quickly right after segmentation) is very valuable to clinicians who often have no time to wait during a procedure. Therefore, making the algorithm run fast and efficiently is vital to the success of the application using such a tool(s) (e.g., via the one or more methods or algorithms discussed herein, via software and/or hardware discussed herein, etc.). Clinicians may have to modify the segmentation by hand, so in such a situation if the medial axis changes accordingly with the segmentation, clinicians have immediate feedback on where to place the probe.

Alternatively or additionally, a medial axis of an object (such as a 3D object) is normally around a center line of the object. Therefore, a center line of an object may also be used to define the target(s) in one or more embodiments. By way of at least one example, a center line may be determined by skeletonizing the object, and such a process may be used to define the target(s) or target zone(s).

After defining the medial axis and the region of interest (e.g., the target zone, the target, etc.) thereof, the medical image, medial line and the border line of the determined region of interest (e.g., the target zone, the target, etc.) may be displayed (e.g., superimposed). A target position may be designated in the displayed image, at which a tip of an ablation device (or other procedural device depending on the procedure being performed by a clinician) is to be positioned, in response to receiving a user input for selecting a position in the displayed medical image.

Figure 9A:
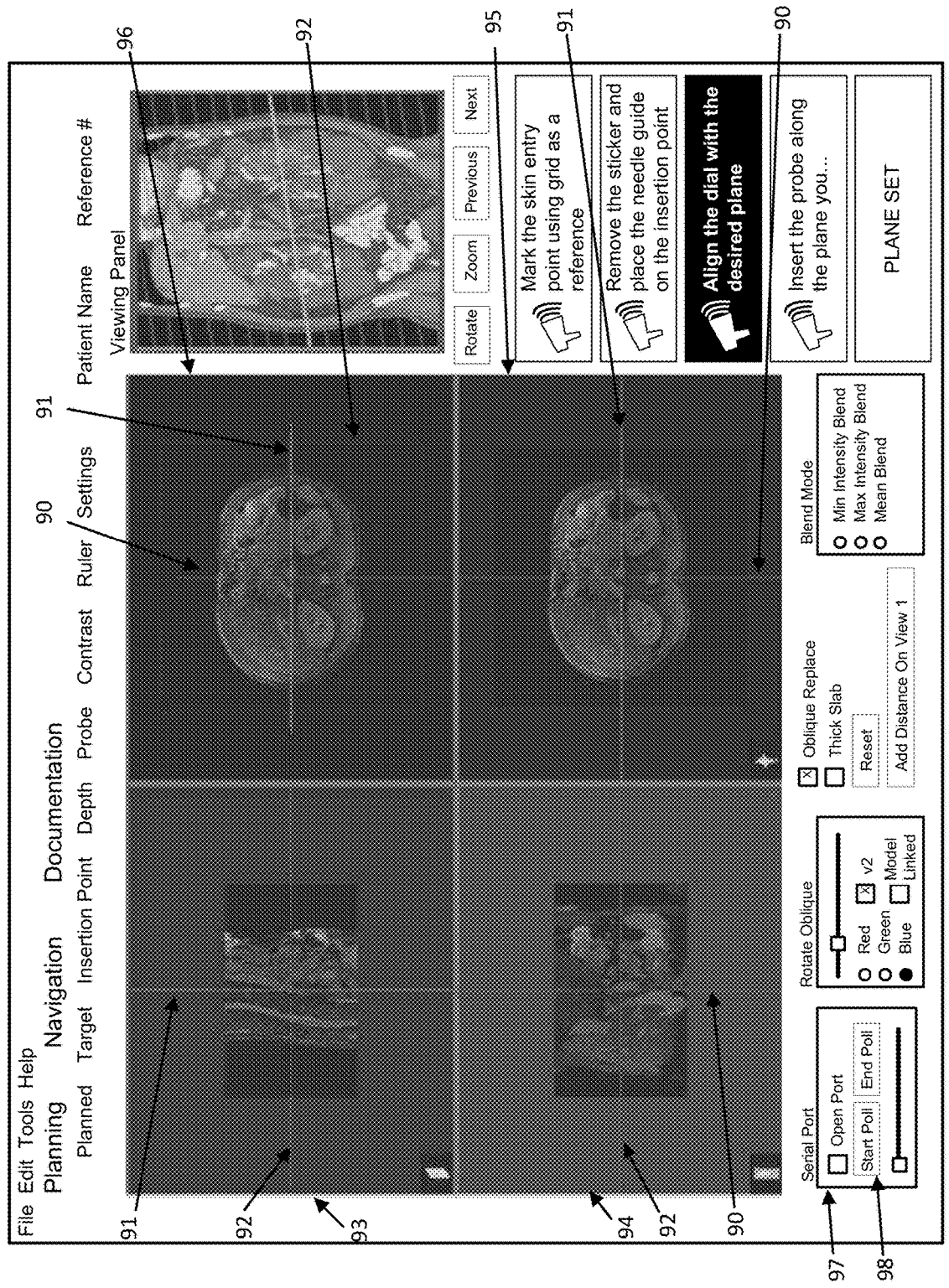
FIGS. 9a-9f are screenshot visual representations of at least one embodiment of a user interface for an ablation planning and/or ablation performing software/platform or process that may be used with a device or system for performing ablation planning and/or ablation in accordance with one or more aspects of the present disclosure.
Figure 9B:
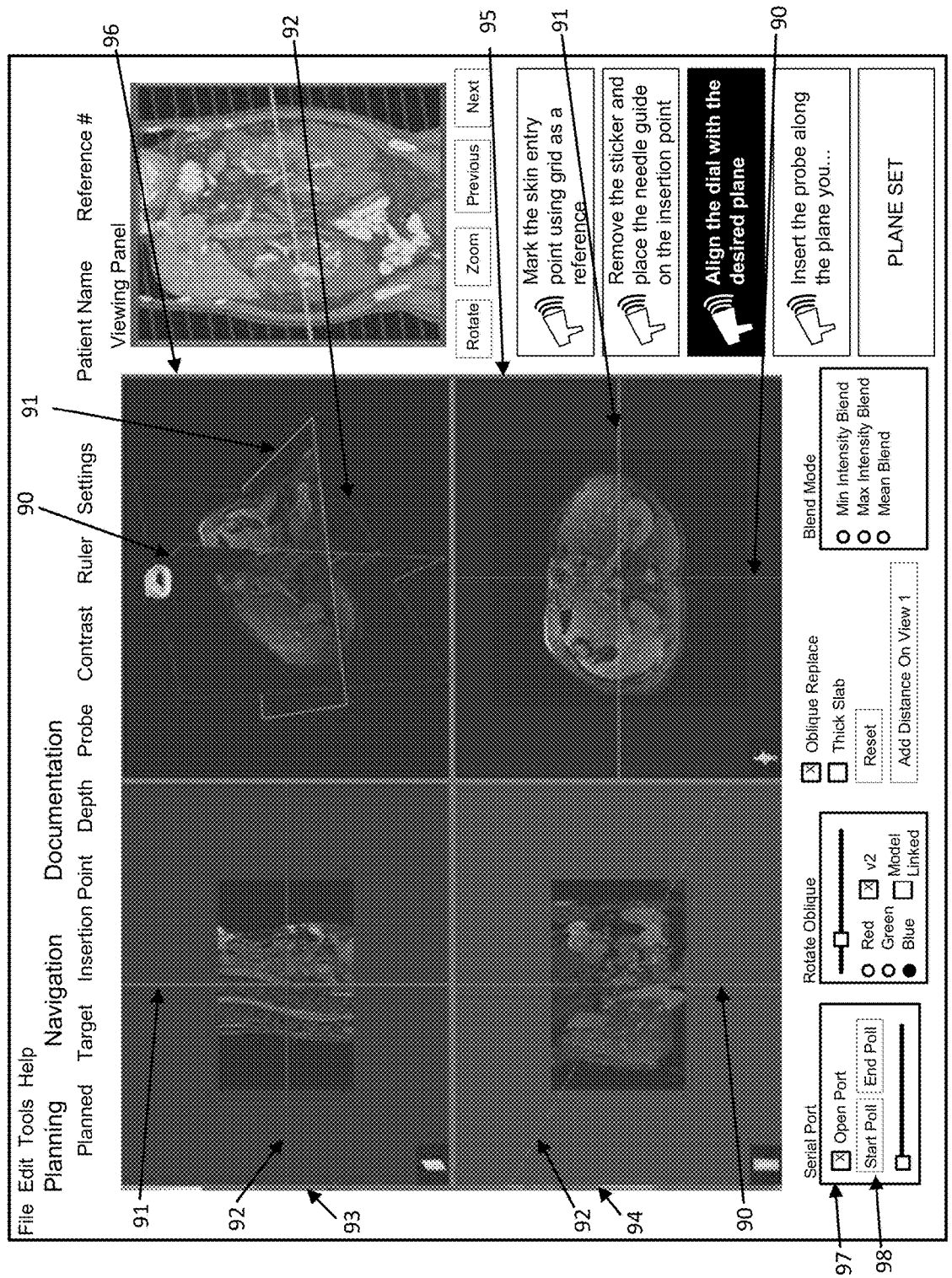
Figure 9C:
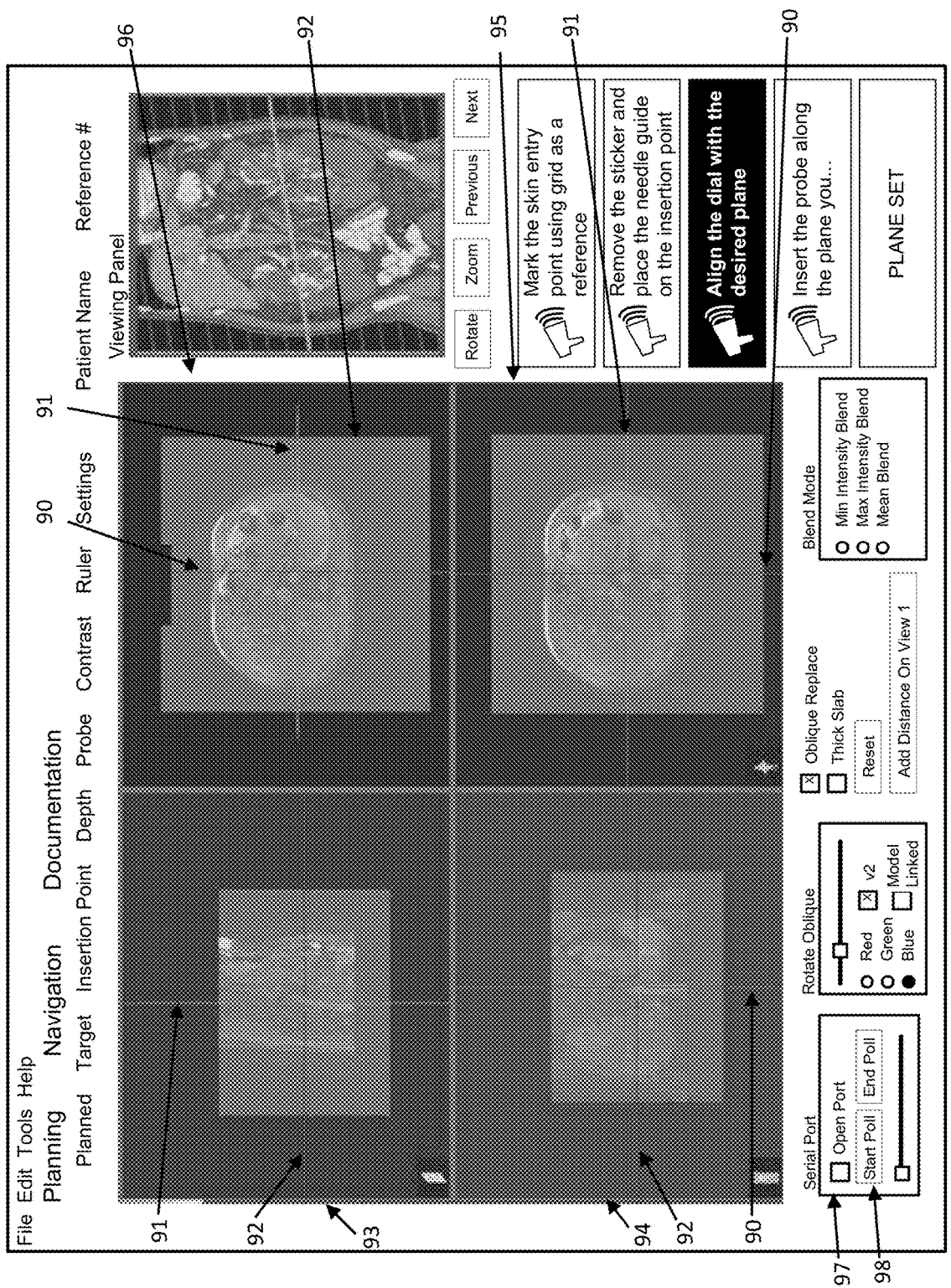
Figure 9D:
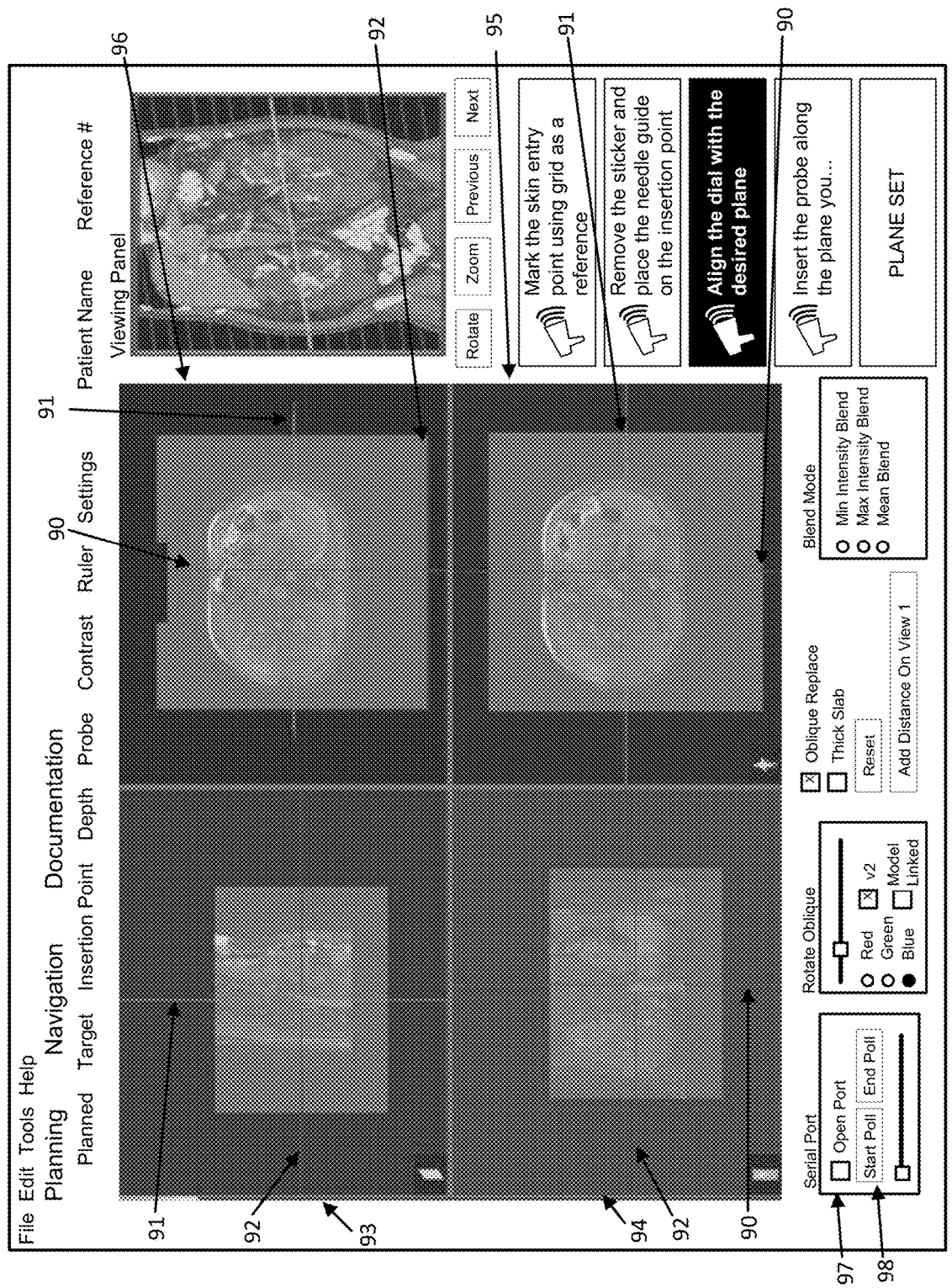
Figure 9E:
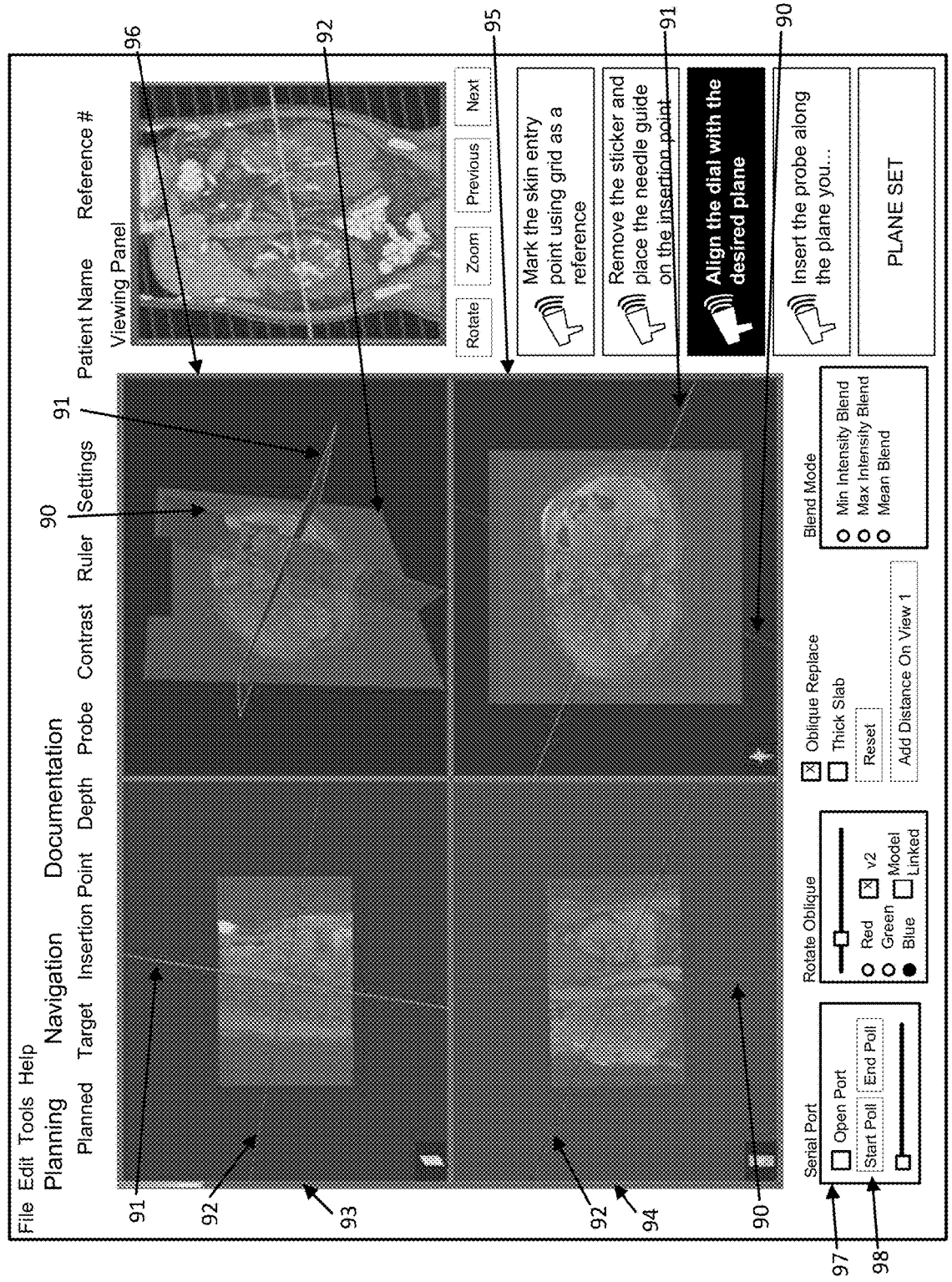
Figure 9F:
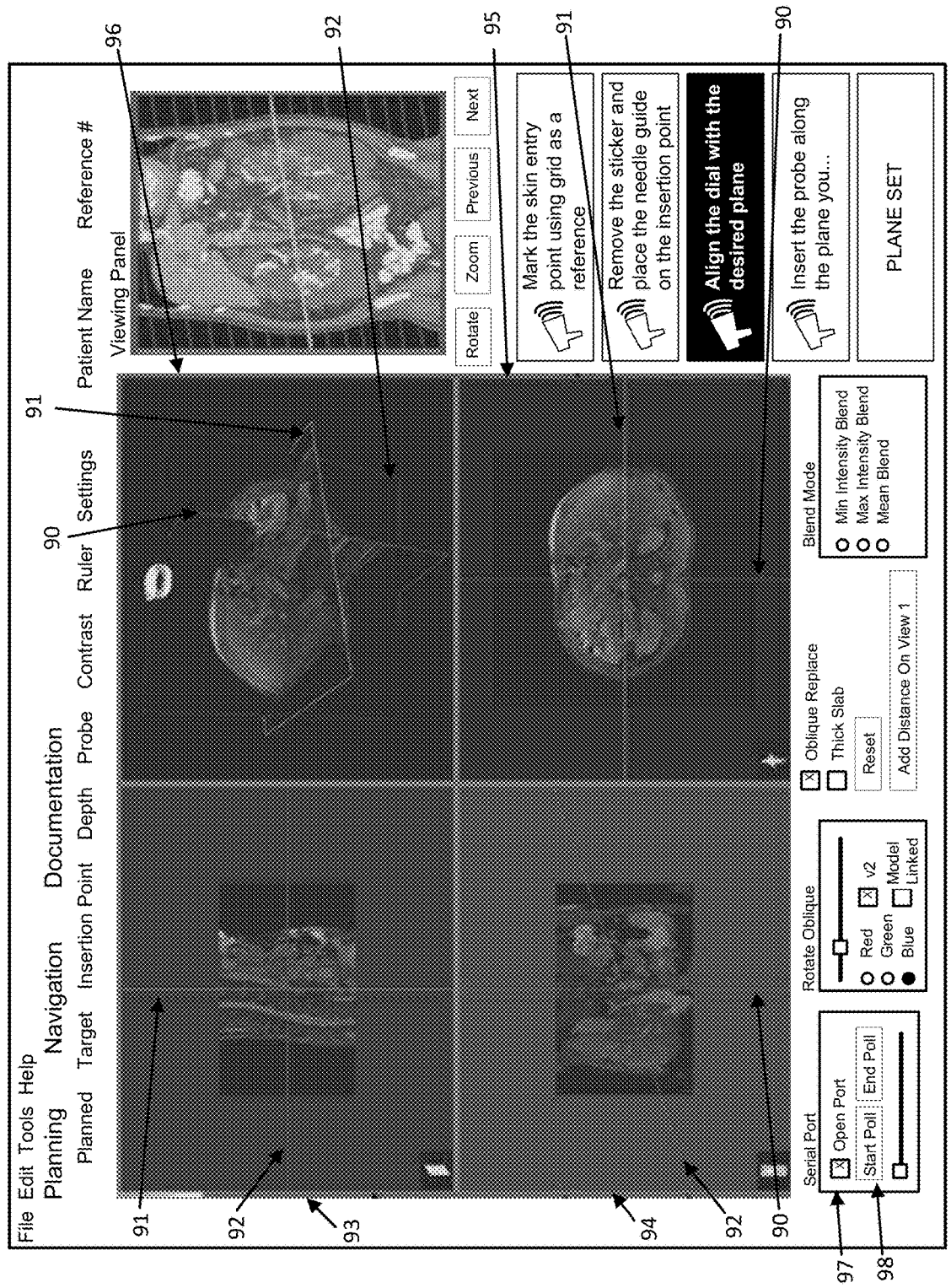
Figure 10:
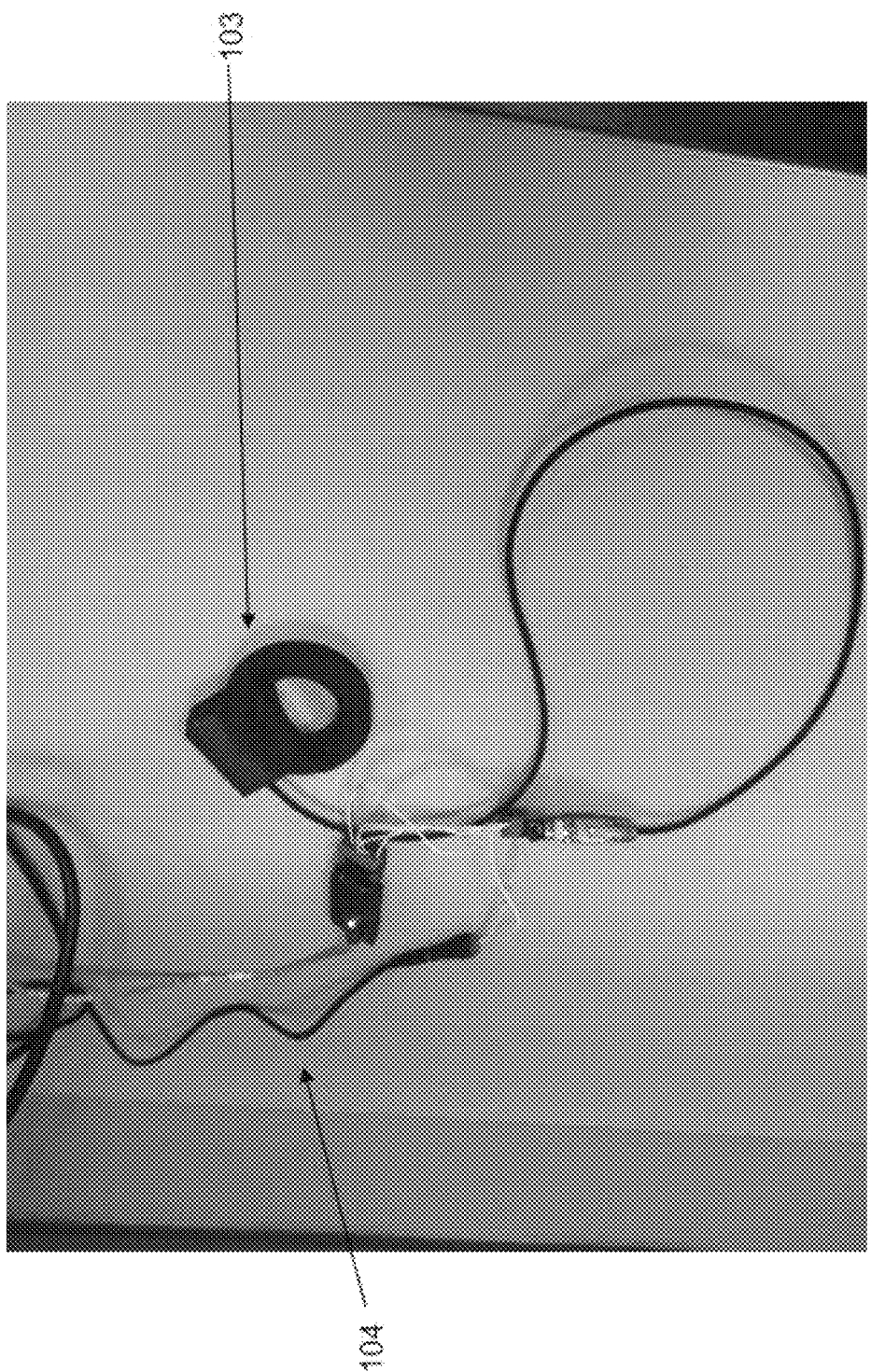
FIG. 10 is an image showing an embodiment of a locator device that may be used with one or more embodiments of an ablation planning and/or ablation performing software/platform, process, device and/or system in accordance with one or more aspects of the present disclosure.
Figure 12A:
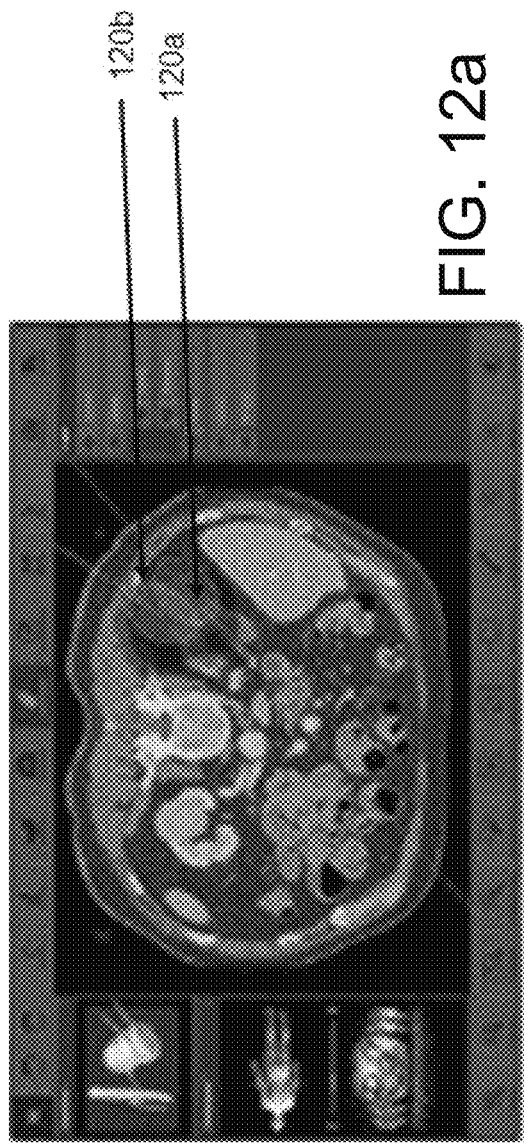
FIGS. 12a-12b are diagrams showing at least one embodiment of multi-probe ablation in accordance with one or more aspects of the present disclosure.
Figure 12B:
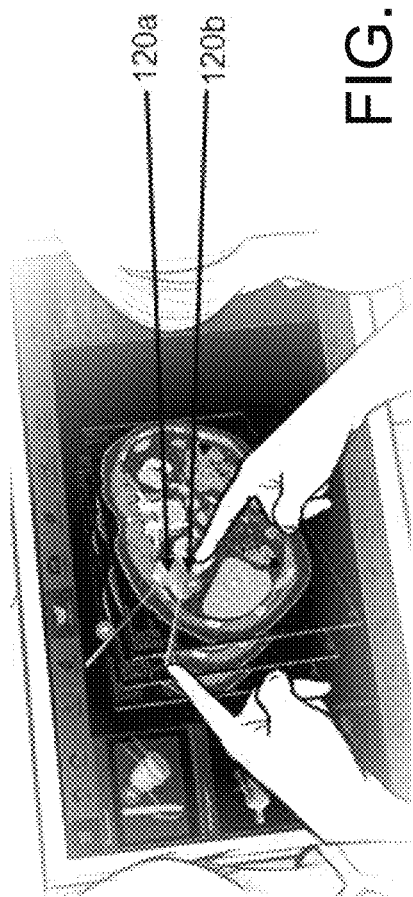

As illustratively shown in FIGS. 9a-9f, software may be used (e.g., in addition or in combination with hardware) to perform the method(s) or algorithm(s) discussed herein. As shown in FIGS. 9a-9f, software for performing ablation planning and ablation performance may include a "Planning" tab and a "Navigation" tab. As shown in FIGS. 9a-9f, the "Navigation" tab may include numerous options for assisting a clinician with ablation planning and/or ablation performance. A viewing panel is provided on the right side of each of FIGS. 9a-9f. On the left and central portions of FIGS. 9a-9f, different images are shown to allow a clinician to view the target or target zone at different axes. FIGS. 9a and 9c-9d show embodiments of the software when launched, and FIGS. 9b and 9e-9f show embodiments of the software during operation when a locator device, such as the device 3 (shown in FIG. 1) or the device 103 (shown in FIG. 10), is placed on a patient. Each of FIGS. 9a-9f have a navigation tab that includes panes (see e.g., panes 93, 94, 95, 96 in FIGS. 9a-9f) showing different aspects of the image. Contrast (or other characteristic(s)) of the image may be increased or decreased (or otherwise modified) via one or more of the panes (such as the panes 93, 94, 95, 96). For example, the image may be shown in the bottom right pane 95. The bottom left pane 94 may show a coronal image. The top left pane 93 may show a sagittal view, and the top right pane 96 may show a 3D view of the image. The cross bars, lines, axes or planes 90, 91, 92 shown in each pane (such as the panes 93, 94, 95, 96) may be used to re-slice the image to show different views thereof, and the 3D image (as shown, for example, in the pane 96) may be rotated or revolved to view different angles or zones of the image. A locator device (e.g., the device 103) may be used to track needle position when one or more needles are being inserted into the patient. Such a locator device (e.g., the device 103) communicates with the system (such as the system 10), and, for example, a computing system (such as the computing system 2 or 2') or processor that is running the software thereon, via a communication interface (see e.g., the cables 104 shown in FIG. 10) that is connected to the computing system (such as the computing system 2 or 2') or processor. Once the locator (such as the device 103) is placed on the patient, the software modifies the displayed axis or axes in the images to provide the clinician or clinicians with an accurate image along the image-plane designated by the positioning of the locator (such as the device 103), and, as aforementioned, the locator (such as the device 103), tracks the one or more needles being used. In one or more embodiments, the locator device (such as the device 103) may be connected to a predetermined port (e.g., a serial port or any other type of port that may be used, such as a USB port) of a computer or computing system (such as the computing system 2 or 2'). The connection to the locator device (such as the device 103) may be established via the software by clicking the "Open Port" box 97 under "Serial Port" so that a computer (such as the computing system 2 or 2') may communicate with each other, and the rotation angle may be fed back into the software application and displayed, for example, as depicted in FIG. 9f (the 3D view in the top right side of the application may be tilted so that the device (such as the device 103) may be seen or seen more clearly). "Start Poll" 98 may be selected by a user to start the locator (such as the device 103) at a predetermined time. The locator (such as the device 103) may be moved to control the slice plane in a corresponding relationship to the movement or modification of the locator (such as the device 103). A user may interact with one or more axes, crossbars, lines or planes (see e.g., lines 90, 91, 92, respectively, as shown in FIGS. 9a-9f (discussed further below)) to get a different slice view. For example, the user may rotate a line bar to obtain a slice view in an oblique direction (see e.g., FIG. 9e). In one or more embodiments, once the Navigation and visualization details have been evaluated (e.g., via the Navigation tab shown in FIGS. 9a-9f), a clinician (e.g., a doctor) may use part of software (e.g., a Planning tab as shown in FIGS. 9a-9f, a user interface as shown in FIGS. 12a-12b, etc.) to set the planning parameters prior to performing the procedure (e.g., ablation). For example, the clinicians may set an optical view, may pick one or more spots in the image(s) from the slice(s) to determine one or more target points, to pick one or more entry points, to determine or set one or more trajectories (e.g., between a target point and an entry point), to drag and drop needles on the image(s), to determine or set how long to perform ablation, to determine or set a power level for ablation, to determine or set the size and shape of the ablation (e.g., iceball, balloon, etc.), etc. After the medial axis or center line is displayed, clinicians may use the medial axis or center line as a reference for insertion of the needle or needles (see e.g., FIGS. 12a-12b further discussed below).

Figure 11:
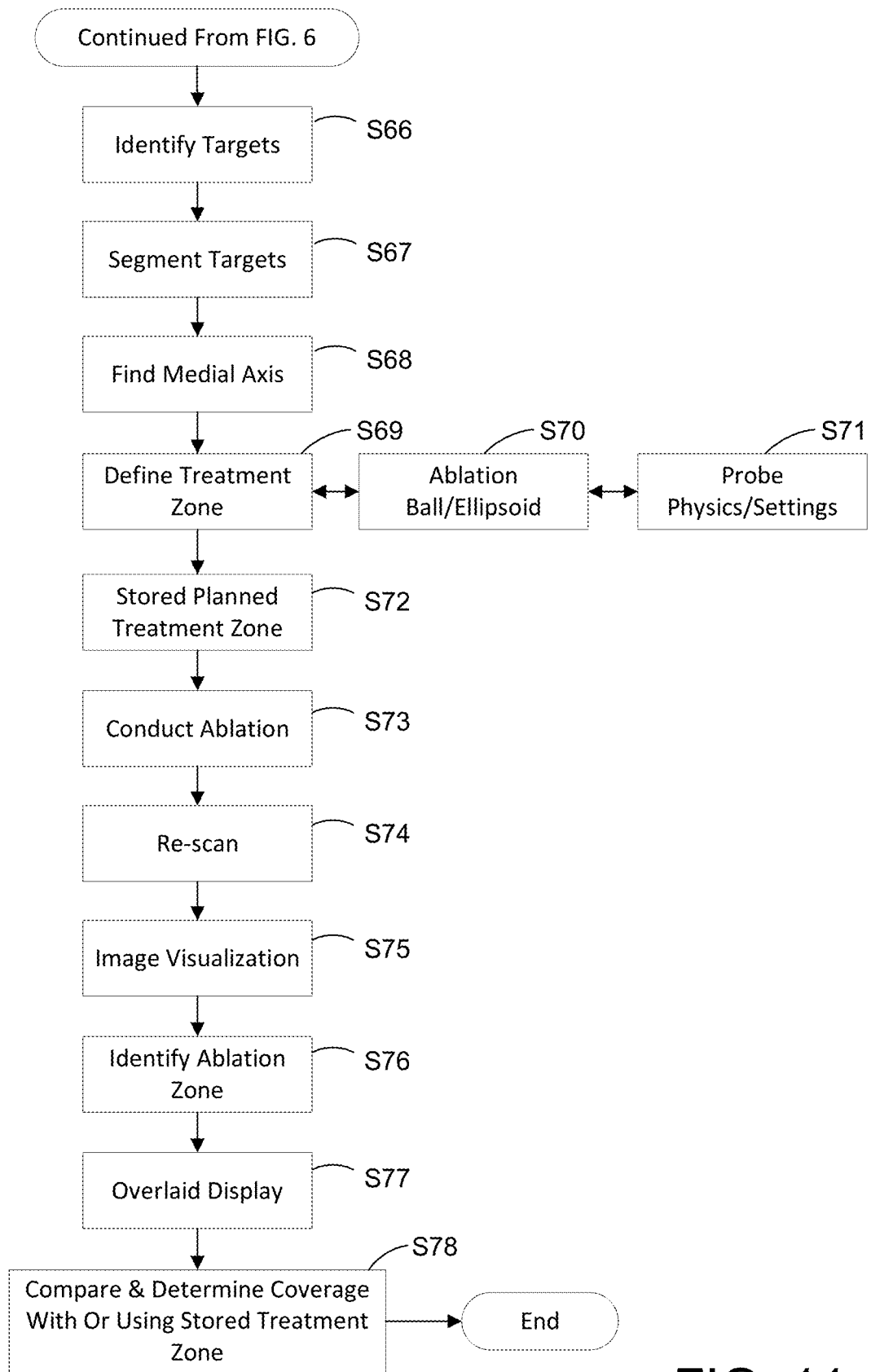
FIG. 11 is a flow chart showing at least another embodiment of a method for performing ablation planning and/or ablation, which in one or more embodiments may be used in combination with other methods disclosed herein (e.g., may be an extension of the method shown in FIG. 6) in accordance with one or more aspects of the present disclosure.

While each of the aforementioned flowcharts has specific steps that may vary from each other, such flowcharts are provided as illustrative embodiment examples, and the steps of the method(s) disclosed herein may be used in various combinations to suit the needs or goals of a particular procedure (e.g., ablation, radiotherapy, etc.) being performed by a predetermined clinician(s). For example, a locator device, such as the locator device 3, may be used with any of the methods disclosed herein, including but not limited to, the margin view methods, the medial axis or center line related methods, etc. The medial axis or center line may be determined for any of the method(s) disclosed herein, including the marginal view method(s), the segmentation steps, the target point and trajectory determination steps, etc. By way of a further example as shown in FIG. 11, the steps of the method shown in FIG. 6 may be continued (see steps S66-S71, which are the same as those steps shown in FIG. 6 and will not be re-described herein) or expanded upon to include additional steps, including, but not limited to: (i) storing a planned treatment zone (see step S72 of FIG. 11); (ii) conducting the predetermined procedure, such as ablation (see step S73 of FIG. 11); (iii) re-scanning the target(s) (see step S74 of FIG. 11); (iv) perform image visualization (e.g., such as by showing multiple panes (views) (e.g., each view may represent a different aspect of the image); as discussed above for step S2 in FIG. 2; as discussed for FIGS. 9a-9f; as otherwise discussed herein; etc.) (see step S75 of FIG. 11); (v) identify the ablation zone (also referred to as the ablated zone or zone that has been subject to ablation) (see step S76 of FIG. 11); (vi) generate the overlaid display (e.g., as shown in FIG. 5 and discussed above regarding the target 51, the ablation or ablated zone 52 and the margin map 53) (see step S77 of FIG. 11); and (vii) compare and determine coverage (for example, via comparison with or using the stored planned treatment zone) (see step S78 of FIG. 11). In one or more embodiments, step S78 may involve, for example, a segmented tumor/lesion region before being ablated being compared with an ablated region to find out if the ablation region covers the tumor or lesion. The comparison of step S78 may be done directly by overlapping two regions from two scans, and/or using a margin map overlapped onto the target (e.g., the tumor/lesion region as shown by the example in FIG. 5). Again, the margin map is the difference between the target (e.g., a tumor/lesion) before ablation and the ablated region after ablation has been performed.

In one or more embodiments, multi-probe or balloon ablation (e.g., as shown in FIGS. 12a-12b) may be used in combination with any feature disclosed herein, including, but not limited to, with a margin map, with a medial axis or center line, with a security or credential check, etc. In one or more embodiments, the size and shape of a biological object, such as a lesion or tumor, may be used to determine whether two or more needles, and two or more probes/balloons, are needed to appropriately ablate a target ablation zone. In one or more embodiments, clinicians may employ a spherical balloon(s) for an ablation zone because it is easy to control. In one or more embodiments, the balloon or balloons may have a different shape, e.g., elliptical or other predetermined shape. Additionally or alternatively, the type of balloon and number of balloons/needles may vary depending on the type of ablation being performed. For example, when performing microwave ablation, RF ablation, laser ablation and/or cryoablation, a spherical balloon may be used or the ablation may require a shape other than spherical. As shown in FIGS. 12a-12b, multi-probe ablation is used with two needles and multiple balloons 120a, 120b to ablate a target ablation zone for a biological object, such as a tumor or lesion. As also shown in FIGS. 12a-12b, the methods disclosed herein may be used to simulate or perform ablation planning when evaluating a biological object or a target/target zone and determining whether to use a two-needle (or more) insertion for ablation.

Figure 13:
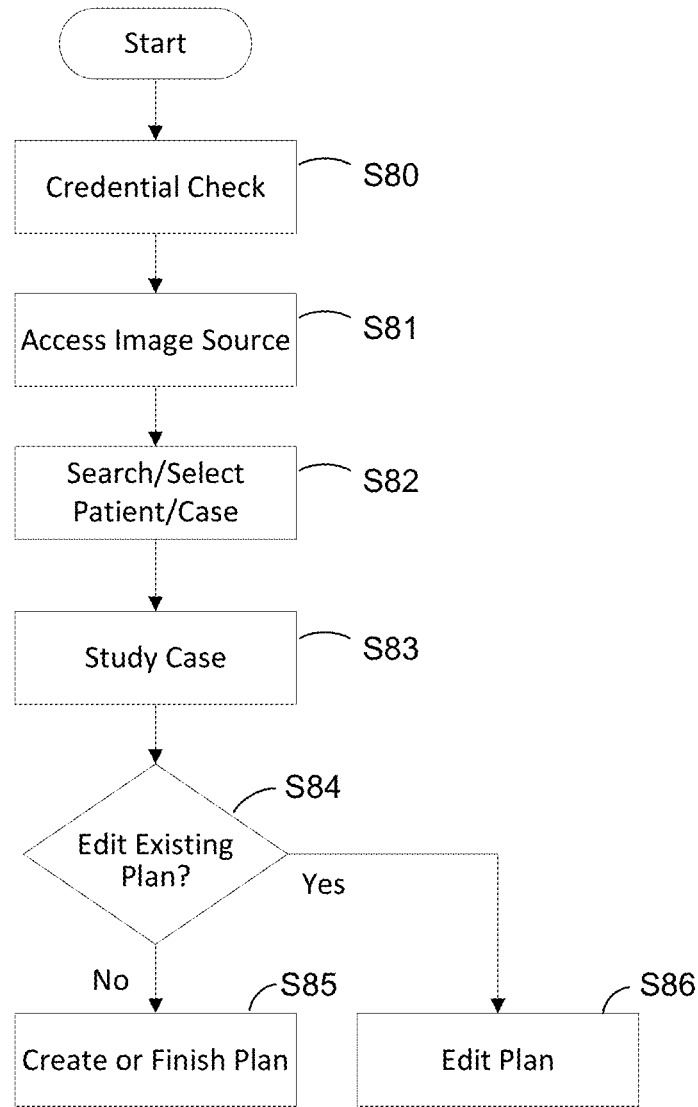
FIG. 13 is a flow chart showing at least another embodiment of a method for performing ablation planning and/or ablation using a security or credential check in accordance with one or more aspects of the present disclosure.

Additionally, in one or more embodiments, a security check may be included to perform the check in the surgical room prior to the ablation procedure to ensure maximal security and safety. To make the security check convenient for clinicians (who have scrubbed in and are wearing gloves at that point and may not be able to use their hands for performing the security check), iris and/or face recognition may be incorporated. Such iris and/or face recognition based approaches may be preferred to control access to patient data (CT scan for example) and communication with peers. While other forms of security control may be used, forms, such as, but not limited to, typing a password, finger print scan, or other forms that require the use of a clinician's hand(s), may not be preferred because a clinician's hands may be sterilized. Once logged in, clinicians may be able to access patient data and communication with peers. FIG. 13 depicts where this checking step may be employed for access image data to create or edit a plan for any medical procedure, such as ablation, cryotherapy, etc. For example, prior to any method disclosed herein for performing ablation planning and/or performance, the credential check (step S80 of FIG. 13) may be performed to make sure that the clinician is permitted to access patient data and communication with other clinicians. Once the clinician passes the credential check (S80), then the clinician has access to the image source (see step S81 of FIG. 13), and may search or select a patient or case file (see step S82 of FIG. 13). Once the patient or case file is retrieved in step S82, the clinician may study the case (see step S83 of FIG. 13), and may determine whether edit(s) to an existing procedure plan (e.g., an ablation plan, a radiotherapy plan, etc.) are required or not (see step S84 in FIG. 13). If "No" edits to an existing plan are needed (e.g., a plan is finished, a plan does not exist, etc.), the clinician may create or finish a plan for the procedure (see step S85 of FIG. 13). If "Yes" and edits to an existing plan are needed, the clinician may edit the previously created plan (see step S86 of FIG. 13). These steps may be used in addition to any of the aforementioned methods for performing ablation planning and/or ablation performance, for radiotherapy planning and/or performance, or other procedural methods as may be useful.

As aforementioned, the methods, devices, systems and storage mediums herein may be used to determine whether or not to edit a procedure plan and/or to evaluate whether the plan or procedure is optimal (e.g., the best option available) or has been successful (and to gauge how successful). This improved ability to measure success is preferred for feedback (such as for the clinician, patient, hospital, other clinicians consulting such results, etc.), and provides an outcome oriented application in one or more embodiments of the present disclosure. For example, as aforementioned, the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion. Hospitals and/or clinicians may further measure the success of a procedure, such as ablation, by whether a lesion or tumor has been successfully removed or destroyed, whether a minimal or reduced number of insertions are used (for instance, additional insertion uses a lot of time and money on handling the needles for the procedure, uses more time and money operating on the insertion of the needle and/or probe, etc.), whether the targeted ablation zone has been ablated successfully, etc. Additionally, one or more embodiments of the present disclosure may contribute to the efficiency and cost reduction of such procedures by assisting clinicians in determining (or determining for clinicians) and defining insertion point(s) for needle placement. Such assistance would greatly reduce or avoid manual work for clinicians. For example, when using the medial axis or center line algorithm(s) or method(s), clinicians may more efficiently determine and define the points for insertion, and may avoid a lengthy and focus-intensive process of determining the insertion points without assistance of such method(s) or algorithm(s). Indeed, the medial axis or center line process is much smaller in range and leads to time saving, especially where such a search needs to go through multiple or numerous slices of an image or images.

In addition to ablation, other procedures, such as radiotherapy, may also benefit from the medial axis or center line method(s) or algorithm(s) discussed herein. Clinicians may use the same concept and software and/or hardware to define where to plant a seed or seeds for radiotherapy, for example.

In at least one embodiment, the computer 2, 2' operates to control the ablation planning and/or ablation performance device(s), system(s) and/or storage medium(s), and may display the scanned image(s) and the procedure plan (e.g., on a monitor or screen such as a display, screen or monitor 1209 as shown in the computer 2 of FIG. 14 and/or the computer 2' of FIG. 15 as further discussed below). The console or processor 2, 2' may be used to control any portions of the system 10 of FIG. 1, for example, including, but not limited to, the ablation device 1, the locator/localizer device 3, the PACS system 4, the CT scanner and console 5, etc. The console 2, 2' may be used to perform any of the aforementioned method(s) or algorithm(s), and may use one or more feature(s) of such method(s) or algorithm(s) in any combination desired by a clinician for a predetermined procedure (e.g., ablation planning and/or performance). For example, the processor 2, 2' may load images (e.g., from a scanner or PACS 4) in step S1 of FIG. 2, and may display such images to allow the clinician to visualize the images (e.g., in step S2 of FIG. 2). The computer, such as the console or computer 2, 2', may receive data from a device (e.g., such as the locator device 103, an image scanner 5, a PACS 4, etc.) or a system via a network interface (see e.g., communication interface 1205 and network 1206 as shown in FIG. 14 or Network I/F 1212 as shown in FIG. 15), or the computer, such as the console or computer 2, 2', may obtain a set of imaging conditions using the operation input from the mouse or keyboard (see e.g., the keyboard 1210 as shown in FIG. 14 or the mouse 1211 and/or keyboard 1210 as shown in FIG. 15).

Unless otherwise discussed herein, like numerals indicate like elements. For example, while variations or differences exist between the methods, devices, systems or storage mediums, such as, but not limited to, the system 10, the methods shown in FIGS. 2-4, 6, 11 and 13, etc., one or more features thereof may be the same or similar to each other, such as, but not limited to, the use of one or more component(s) thereof (e.g., the console 2, the console 2', the ablation device 1, the locator/localizer device 3, the PACS 4, the CT scanner 5, etc.). Those skilled in the art will appreciate that the method steps disclosed herein may operate in the same or similar fashion to those like-numbered elements of one or more other methods or algorithms as discussed herein. Those skilled in the art will appreciate that alternative embodiments of the system 10, may be used while having other variations as discussed herein for performing one or more methods discussed herein. Likewise, while the console or computer 2 may be used in one or more systems or with one or more methods disclosed herein, one or more other consoles or computers, such as the console or computer 2', may be used additionally or alternatively.

There are many ways to plan for and perform ablation or any other measurement or determination discussed herein, digital as well as analog. In at least one embodiment, a computer, such as the console or computer 2, 2', may be dedicated to control and monitor the devices, systems, methods and/or storage mediums described herein.

Figure 14:
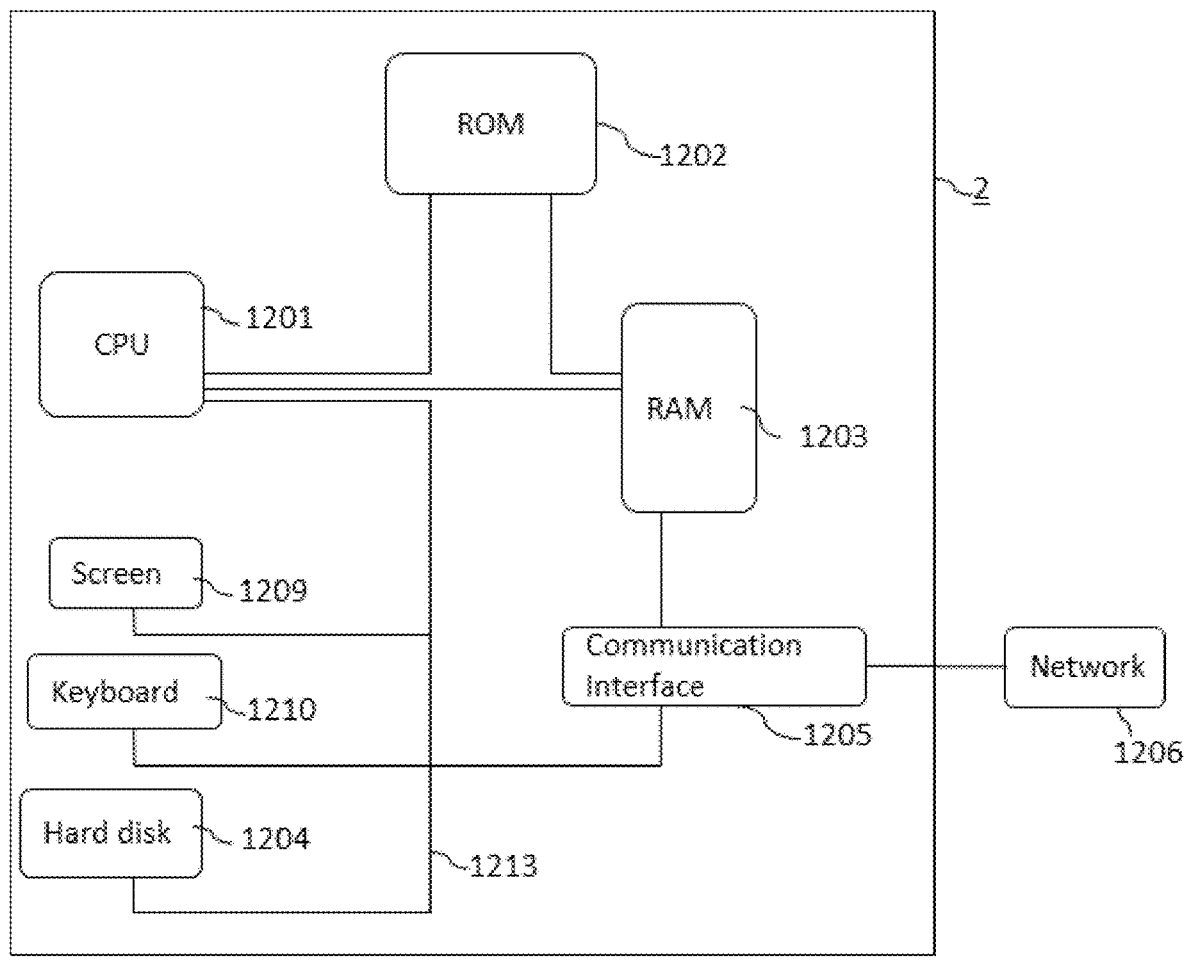
FIG. 14 shows a schematic diagram of an embodiment of a computer that may be used with one or more embodiments of an ablation planning and/or performance method, apparatus or system in accordance with one or more aspects of the present disclosure.
Figure 15:
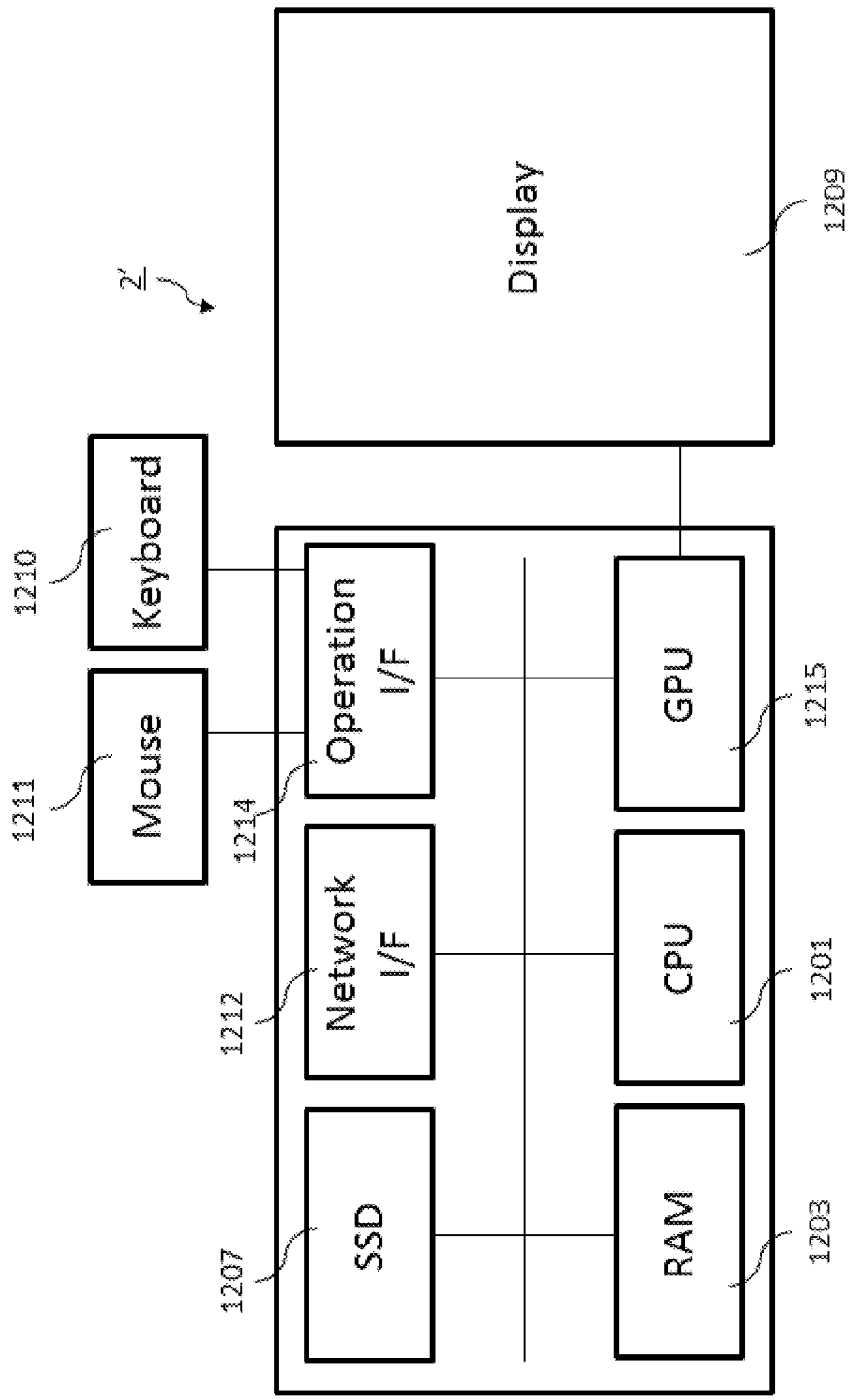
FIG. 15 shows a schematic diagram of another embodiment of a computer that may be used with one or more embodiments of an ablation planning and/or performance method, apparatus or system in accordance with one or more aspects of the present disclosure.

Various components of a computer system 2 (see e.g., the console or computer 2 as shown in FIG. 1) are provided in FIG. 14. A computer system 2 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 1). In addition, the computer system 2 may comprise one or more of the aforementioned components. For example, a computer system 2 may include a CPU 1201, a RAM 1203, an input/output (I/O) interface (such as the communication interface 1205) and a bus (which may include one or more lines 1213 as a communication system between components of the computer system 2; in one or more embodiments, the computer system 2 and at least the CPU 1201 thereof may communicate with the one or more aforementioned components of an ablation performance and/or planning device or system, such as, but not limited to, the system 10 discussed herein above, via one or more lines 1213), and one or more other computer systems 2 may include one or more combinations of the other aforementioned components. The CPU 1201 is configured to read and perform computer-executable instructions stored in a storage medium. The computer-executable instructions may include those for the performance of the methods and/or calculations described herein. The system 2 may include one or more additional processors in addition to CPU 1201, and such processors, including the CPU 1201, may be used for performing ablation planning and/or performance. The system 2 may further include one or more processors connected via a network connection (e.g., via network 1206). The CPU 1201 and any additional processor being used by the system 2 may be located in the same telecom network or in different telecom networks (e.g., performing ablation planning and/or performance technique(s) may be controlled remotely).

The I/O or communication interface 1205 provides communication interfaces to input and output devices, which may include the ablation device 1, the locator/localizer 3, the PACS 4, the CT scanner 5, a microphone, a communication cable and a network (either wired or wireless), a keyboard 1210, a mouse (see e.g., the mouse 1211 as shown in FIG. 15), a touch screen or screen 1209, a light pen and so on. The Monitor interface or screen 1209 provides communication interfaces thereto.

Any methods and/or data of the present disclosure, such as the methods for performing ablation planning and/or performance, radiotherapy, or otherwise as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 12), SRAM, etc.), an optional combination thereof, a server/database, etc. may be used to cause a processor, such as, the processor or CPU 1201 of the aforementioned computer system 2 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 2, etc., as described above may be achieved utilizing suitable hardware, such as that illustrated in the figures. Functionality of one or more aspects of the present disclosure may be achieved utilizing suitable hardware, such as that illustrated in FIG. 14 or FIG. 15. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 14 or 15) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 2' is shown in FIG. 15. The computer 2' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 2' includes a display 1209. The computer 2' may connect with the ablation device 1, the locator/localizer device 3, the PACS 4, the CT scanner 5, communication devices (e.g., to discuss the procedure with peers, clinicians, etc.) via the operation interface 1214 or the network interface 1212. The operation interface 1214 is connected with an operation unit such as a mouse device 1211, a keyboard 1210 or a touch panel device. The computer 2' may include two or more of each component.

In at least one embodiment, a computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 2, 2', communicates with one or more other system components (e.g., the ablation device 1, the locator/localizer device 3, the PACS 4, the CT scanner 5 or other type of scanner, of system 10 or other device or system being used for ablation planning and/or performance) to perform imaging, planning and/or performance. The monitor or display 1209 displays the plan and performance steps (e.g., in real time), and may display other information about the imaging condition or about an object to be imaged and operated on during the procedure. The monitor 1209 also provides a graphical user interface for a user to operate an ablation planning and/or performance device or system (e.g., the system 10). An operation signal is input from the operation unit (e.g., such as, but not limited to, a mouse device 1211, a keyboard 1210, a touch panel device, etc.) into the operation interface 1214 in the computer 2', and corresponding to the operation signal the computer 2' instructs the system (e.g., the system 10) to set or change the imaging, planning and/or performance condition(s), and to start or end any portion of any of the method(s) discussed herein.

The present disclosure and/or one or more components of devices, systems and storage mediums, and/or methods, thereof also may be used in conjunction with any suitable optical assembly including, but not limited to, probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,557,154 and Patent Application Publication Nos. US2017/0035281; WO2015/116951; WO2015/116939; and WO2017/024145 and U.S.

Non-Provisional patent application Ser. No. 15/418,329 filed Jan. 27, 2017 which published as U.S. Pat. Pub. No. 2018/0017778, each of which patents and patent publications are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374 and 2016/0228097, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. A method for performing ablation simulation or performance, or ablation planning and ablation simulation or performance, using an image processing apparatus having one or more processors, the method comprising:

visualizing or displaying, via the one or more processors, at least one image;

automatically identifying, by the one or more processors, at least one treating zone or target shown in the at least one image such that: (i) the one or more processors calculate and determine the at least one treating zone or target shown in the at least one image, or (ii) the one or more processors determine the at least one treating zone or target shown in the at least one image by processing and analyzing the at least one image;

determining or calculating, via the one or more processors, a medial axis or a center line of the at least one treating zone or target;

visualizing or displaying, on a display via the one or more processors, the determined or calculated medial axis or the determined or calculated center line and the at least one treating zone or target being superimposed on or displayed in the at least one image, the determined or calculated medial axis or the determined or calculated center line defining a plurality of target point candidates;

receiving an input, based on or using the superimposed or displayed medial axis or center line on the display via the one or more processors, the input operating to select, designate, or define at least one target point of the plurality of target point candidates to be at least one position on the determined or calculated medial axis or on the determined or calculated center line;

defining, via the one or more processors, the at least one target point of the plurality of target point candidates of the at least one treating zone or target based on the received input, at least one entry point, and a trajectory between the at least one target point and the at least one entry point, the at least one target point of the at least one treating zone or target being defined located or positioned on the determined or calculated medial axis or the determined or calculated center line of the at least one treating zone or target;

corresponding or associating, via the one or more processors, the at least one entry point in the at least one image to at least one entry point for a body of a patient; and performing the ablation simulation or performance, or the ablation planning and ablation simulation or performance, on the at least one treating zone or target based on the at least one target point such that ablation is simulated with a needle located at or on the target point or ablation is activated with the needle located at or on the target point, the at least one target point operating to define and position a simulation or performance zone, or a planning and simulation or performance zone, to be used to perform the ablation simulation or performance, or the ablation planning and the ablation simulation or performance, on the at least one treating zone or target.

2. The method of claim 1, wherein the at least one image is loaded from at least one of the following: a scanner, a PACS, an image reader or reading device, an imaging device, and a medical imaging device or system.

3. The method of claim 1, wherein at least one of:
(i) the at least one image is displayed in one or more panes; and
(ii) the one or more panes include at least one of: an axial view pane, a coronal view pane, a sagittal view pane, and a three dimensional (3D) view pane.

4. The method of claim 1, further comprising identifying, via the one or more processors, the at least one treating zone or target using at least one of: image segmentation, an active contour model, a snake algorithm, and a watershed method.

5. The method of claim 1, further comprising using a calibration device to at least one of: (i) help correspond or associate the at least one entry point to the entry point for the body of the patient; and (ii) help determine the medial axis or the center line of the at least one treating zone or target.

6. The method of claim 1, further comprising performing, via the one or more processors, segmentation, registration, and differential image view steps to provide improved differential image(s) and to reduce or avoid generation of misleading artifacts in the image(s).

7. The method of claim 1, wherein the performing of the ablation simulation or performance, or the ablation planning and the ablation simulation or performance, includes performing an ablation step or includes performing an incremental step and an ablation step.

8. The method of claim 7, further comprising:
identifying or determining, via the one or more processors, whether the simulation or performance zone, or the planning and the simulation or performance zone, of the ablation simulation or performance, or the ablation planning and the ablation simulation or performance, corresponds to an ablation or ablated zone where an ablation occurred in response to the ablation step being performed such that the ablation or ablated zone covers the at least one treating zone or target, and
in a case where the ablation or ablated zone covers the at least one treating zone or target, stopping the ablation step, or, in a case where the ablation or ablated zone does not cover the at least one treating zone or target, performing another ablation step until the ablation or ablated zone covers the at least one treating zone or target.

9. The method of claim 7, further comprising, in response to the incremental step being performed:
(i) scanning or re-scanning the at least one image;
(ii) displaying, visualizing, or re-visualizing, via the one or more processors, the scanned or re-scanned at least one image;
(iii) confirming, via the one or more processors, the at least one treating zone or target is the same or identifying, via the one or more processors, an updated or changed at least one treating zone or target;
(iv) segmenting, via the one or more processors, the scanned or re-scanned at least one image;
(v) performing, via the one or more processors, image registration of the at least one image;
(vi) performing, via the one or more processors, differentiation of the scanned or re-scanned at least one image to obtain a differential margin; and
(vii) overlaying, via the one or more processors, the differential margin on the at least one image to generate or form a margin map.

10. The method of claim 1, further comprising performing, via the one or more processors, a simulation step.

11. The method of claim 10, wherein the simulation step includes at least one of: simulating an ablation zone for the ablation simulation, simulating an ice ball for cryoablation for the ablation simulation, simulating a balloon for microwave ablation for the ablation simulation, and simulating or mimicking tissue deformation or movement of the patient.

12. The method of claim 11, further comprising changing a shape or location of the medial axis or the center line of the at least one treating zone or target to simulate or mimic tissue deformation or movement.

13. The method of claim 1, further comprising performing, via the one or more processors, a medial axis algorithm or using one or more centers of one or more maximally-inscribed balls inside the treating zone or target to identify the medial axis or the center line of the at least one treating zone or target.

14. The method of claim 1, further comprising:
storing, via the one or more processors, a planned treatment zone for the at least one treating zone or target;
identifying, via the one or more processors, an ablation or ablated zone after ablation is performed on the treating zone or target; and
displaying, via the one or more processors, an overlaid image of the at least one treating zone or target and the ablation or ablated zone to generate a margin map.

15. The method of claim 14, further comprising comparing, via the one or more processors, the stored planned treatment zone for the at least one treating zone or target with the ablation or ablated zone to determine whether the ablation or ablated zone covers the at least one treating zone or target.

16. A computer-readable storage medium storing a program that operates to cause one or more processors to execute a method for performing ablation simulation or performance, or for performing ablation planning and ablation simulation or performance, the method comprising:
visualizing or displaying at least one image;
automatically identifying at least one treating zone or target shown in the at least one image such that: (i) the one or more processors calculate and determine the at least one treating zone or target shown in the at least one image, or (ii) the one or more processors determine the at least one treating zone or target shown in the at least one image by processing and analyzing the at least one image;
determining or calculating a medial axis or a center line of the at least one treating zone or target;
visualizing or displaying, on a display, the determined or calculated medial axis or the determined or calculated center line and the at least one treating zone or target being superimposed on or displayed in the at least one image, the determined or calculated medial axis or the determined or calculated center line defining a plurality of target point candidates;
receiving an input, based on or using the superimposed or displayed medial axis or center line on the display, the input operating to select, designate, or define at least one target point of the plurality of target point candidates to be at least one position on the determined or calculated medial axis or on the determined or calculated center line;
defining the at least one target point of the plurality of target point candidates of the at least one treating zone or target based on the received input, at least one entry point, and a trajectory between the at least one target point and the at least one entry point, the at least one target point of the at least one treating zone or target being located or positioned on the determined or calculated medial axis or a on the determined or calculated center line of the at least one treating zone or target;
corresponding or associating the at least one entry point in the at least one image to at least one entry point for a body of a patient; and
performing the ablation simulation or performance, or the ablation planning and ablation simulation or performance, on the at least one treating zone or target based on the at least one target point such that ablation is simulated with a needle located at or on the target point or ablation is activated with the needle located at or on the target point, the at least one target point operating to define and position a simulation or performance zone, or a planning and simulation or performance zone, to be used to perform the ablation simulation or performance, or the ablation planning and the ablation simulation or performance, on the at least one treating zone or target.

* * * * *